(12) United States Patent
Patterson et al.

(10) Patent No.: US 10,226,489 B2
(45) Date of Patent: Mar. 12, 2019

(54) COMPOSITION OF BACTEROIDES THETAIOTAOMICRON FOR IMMUNE MODULATION

(71) Applicant: 4D PHARMA RESEARCH LIMITED, Aberdeen (GB)

(72) Inventors: Angela Margaret Patterson, Norwich (GB); George Grant, Aberdeen (GB); Imke Mulder, Aberdeen (GB)

(73) Assignee: 4D Pharma Research Limited (GB)

( * ) Notice: Subject to any disclaimer, the term of this patent is extended or adjusted under 35 U.S.C. 154(b) by 0 days.

(21) Appl. No.: 15/631,945

(22) Filed: Jun. 23, 2017

(65) Prior Publication Data

US 2017/0326184 A1 Nov. 16, 2017

Related U.S. Application Data

(63) Continuation of application No. PCT/GB2015/054112, filed on Dec. 22, 2015.

(51) Int. Cl.

| C12N 1/04 | (2006.01) |
| A61K 35/74 | (2015.01) |
| A23L 33/135 | (2016.01) |
| C12R 1/01 | (2006.01) |
| A61K 9/00 | (2006.01) |
| A61K 9/19 | (2006.01) |

(52) U.S. Cl.
CPC ............ *A61K 35/74* (2013.01); *A23L 33/135* (2016.08); *A61K 9/0053* (2013.01); *A61K 9/19* (2013.01); *C12N 1/04* (2013.01); *C12R 1/01* (2013.01); *A23V 2002/00* (2013.01)

(58) Field of Classification Search
None
See application file for complete search history.

(56) References Cited

U.S. PATENT DOCUMENTS

| 4,683,202 A | 7/1987 | Mullis |
| 5,589,168 A | 12/1996 | Allen et al. |
| 5,925,657 A | 7/1999 | Seed et al. |
| 7,749,494 B2 | 7/2010 | Renaud et al. |
| 7,998,474 B2 | 8/2011 | Kelly |
| 8,460,648 B2 | 6/2013 | Borody |
| 9,011,834 B1 | 4/2015 | McKenzie et al. |
| 9,314,489 B2 | 4/2016 | Kelly et al. |
| 9,371,510 B2 * | 6/2016 | Moore .................... C12N 1/20 |
| 9,376,473 B2 | 6/2016 | Gleiberman et al. |
| 9,539,293 B2 | 1/2017 | Kelly et al. |
| 9,610,307 B2 | 4/2017 | Berry et al. |
| 9,662,381 B2 | 5/2017 | Honda et al. |
| 9,796,762 B2 | 10/2017 | Kelly et al. |
| 9,808,519 B2 | 11/2017 | Honda et al. |
| 9,974,815 B2 | 5/2018 | Mulder et al. |
| 9,987,311 B2 | 6/2018 | Mulder et al. |
| 2003/0147858 A1 | 8/2003 | Renaud et al. |
| 2006/0073161 A1 | 4/2006 | Breton |
| 2007/0286913 A1 | 12/2007 | Swain et al. |
| 2008/0069861 A1 | 3/2008 | Brown et al. |
| 2010/0284973 A1 | 11/2010 | Schiffer-Mannioui et al. |
| 2010/0303782 A1 | 12/2010 | Cobb et al. |
| 2010/0311686 A1 | 12/2010 | Kasper et al. |
| 2010/0316617 A1 | 12/2010 | Renaud et al. |
| 2011/0086011 A1 | 4/2011 | Kasper et al. |
| 2013/0195802 A1 | 8/2013 | Moore |
| 2014/0037716 A1 | 2/2014 | Nowill et al. |
| 2014/0147425 A1 | 5/2014 | Henn et al. |
| 2014/0154218 A1 | 6/2014 | Kohno et al. |
| 2014/0199281 A1 | 7/2014 | Henn et al. |
| 2014/0335131 A1 | 11/2014 | Mazmanian et al. |
| 2014/0341921 A1 | 11/2014 | Honda et al. |
| 2015/0071957 A1 | 3/2015 | Kelly et al. |
| 2015/0104418 A1 | 4/2015 | Flint et al. |
| 2016/0067188 A1 | 3/2016 | Cade et al. |
| 2016/0184370 A1 | 6/2016 | McKenzie et al. |
| 2016/0199424 A1 | 7/2016 | Berry et al. |
| 2016/0279177 A1 | 9/2016 | Kelly et al. |
| 2017/0143772 A1 | 5/2017 | Mulder et al. |
| 2017/0143773 A1 | 5/2017 | Mulder et al. |
| 2017/0143774 A1 | 5/2017 | Mulder et al. |
| 2017/0143775 A1 | 5/2017 | Mulder et al. |
| 2017/0173089 A1 | 6/2017 | Kelly |
| 2017/0354695 A1 | 12/2017 | Grant et al. |
| 2017/0360856 A1 | 12/2017 | Grant et al. |

(Continued)

FOREIGN PATENT DOCUMENTS

| CN | 101590081 A | 12/2009 |
| CN | 102940652 A | 2/2013 |
| CN | 103156888 A | 6/2013 |

(Continued)

OTHER PUBLICATIONS

Wrzosek et al. BMC Biology 2013, 11:61, pp. 1-13.*
ATCC Catalog, https://www.atcc.org/Search_Results.aspx? dsNav=Ntk:PrinnarySearch%7cBacteroides+thetaiotaonnicron%7c3%7c,Ny:True,Ro:0,N:1000552&searchTerms=Bacteroides+thetaiotaonnicron&redir=1, accessed May 2, 2018.*
Kelly et al., Trends in Immunology vol. 26 No. 6 Jun. 2005.*
Barry et al., Journal of Clinical Microbiology. Jan. 1988, p. 13-17.*
Falony et al., Applied and Environmental Microbiology, Apr. 2009, p. 2312-2319 vol. 75, No. 8.*
Yu et al., Glycobiology vol. 23 No. 11 pp. 1281-1292, 2013.*
Altschul et al. 'Basic local alignment search tool.' Journal of Molecular Biology. 1990, vol. 215, No. 3, pp. 403-410.
An et al. (1985) "New cloning vehicles for transformation of higher plants," EMBO J. 4:277-284.

(Continued)

*Primary Examiner* — Irene Marx
(74) *Attorney, Agent, or Firm* — Wilson Sonsini Goodrich & Rosati

(57) ABSTRACT

The present invention provides a strain of *Bacteroides thetaiotaomicron* and derivatives thereof, and the use of said strain or derivatives in treating inflammatory, autoimmune and allergic disorders. The invention also provides pharmaceutical compositions, nutritional supplements, feedstuffs, food products, dietary supplements, and food additives comprising said strain or derivatives.

14 Claims, 12 Drawing Sheets

Specification includes a Sequence Listing.

(56) References Cited

U.S. PATENT DOCUMENTS

2017/0368110 A1 12/2017 Grant et al.

FOREIGN PATENT DOCUMENTS

| | | |
|---|---|---|
| CN | 103652322 A | 3/2014 |
| CN | 103981115 A | 8/2014 |
| CN | 102940652 B | 3/2015 |
| CN | 104546932 A | 4/2015 |
| CN | 104546933 A | 4/2015 |
| CN | 104546934 A | 4/2015 |
| CN | 104546935 A | 4/2015 |
| CN | 104546940 A | 4/2015 |
| CN | 104546942 A | 4/2015 |
| EP | 1448995 A1 | 8/2004 |
| EP | 2687227 A1 | 1/2014 |
| EP | 2810652 A2 | 12/2014 |
| EP | 2832859 A1 | 2/2015 |
| JP | H08259450 A | 10/1996 |
| JP | 2003261453 A | 9/2003 |
| JP | 2005097280 A | 4/2005 |
| JP | 2007084533 A | 4/2007 |
| JP | 2007116991 A | 5/2007 |
| JP | 2009507023 A | 2/2009 |
| JP | 2010246523 A | 11/2010 |
| JP | 2013527240 A | 6/2013 |
| JP | 2015500792 A | 1/2015 |
| KR | 20100128168 A | 12/2010 |
| WO | WO-9117243 A1 | 11/1991 |
| WO | WO-9843081 A1 | 10/1998 |
| WO | WO-9857631 A1 | 12/1998 |
| WO | WO-9919459 A1 | 4/1999 |
| WO | WO-9945955 A1 | 9/1999 |
| WO | WO-01016120 A1 | 3/2001 |
| WO | WO-0185187 A1 | 11/2001 |
| WO | WO-03046580 A1 | 6/2003 |
| WO | WO-2007027761 A2 | 3/2007 |
| WO | WO-2007136719 A2 | 11/2007 |
| WO | WO-2008055703 A2 | 5/2008 |
| WO | WO-2009027753 A1 | 3/2009 |
| WO | WO-2009072889 A1 | 6/2009 |
| WO | WO-2009154463 A2 | 12/2009 |
| WO | WO-2011110918 A1 | 9/2011 |
| WO | WO-2011149335 A1 | 12/2011 |
| WO | WO-2011152566 A2 | 12/2011 |
| WO | WO-2011153226 A2 | 12/2011 |
| WO | WO-2012024638 A2 | 2/2012 |
| WO | WO-2011153226 A3 | 3/2012 |
| WO | WO-2012142605 A1 | 10/2012 |
| WO | WO-2013008039 A2 | 1/2013 |
| WO | WO-2013037068 A1 | 3/2013 |
| WO | WO-2013050792 A1 | 4/2013 |
| WO | WO-2013080561 A1 | 6/2013 |
| WO | WO-2013124725 A1 | 8/2013 |
| WO | WO-2014001368 A1 | 1/2014 |
| WO | WO-2014067976 A1 | 5/2014 |
| WO | WO-2014075745 A1 | 5/2014 |
| WO | WO-2014078911 A1 | 5/2014 |
| WO | WO-2014121298 A2 | 8/2014 |
| WO | WO-2014121304 A1 | 8/2014 |
| WO | WO-2014137211 A1 | 9/2014 |
| WO | WO-2014145958 A2 | 9/2014 |
| WO | WO-2014152338 A1 | 9/2014 |
| WO | WO-2014167338 A1 | 10/2014 |
| WO | WO-2014201037 A2 | 12/2014 |
| WO | WO-2015006355 A2 | 1/2015 |
| WO | WO-2015013214 A2 | 1/2015 |
| WO | WO-2015021936 A1 | 2/2015 |
| WO | WO-2015095241 A2 | 6/2015 |
| WO | WO-2015156419 A1 | 10/2015 |
| WO | WO-2015156519 A1 | 10/2015 |
| WO | WO-2015169944 A1 | 11/2015 |
| WO | WO-2016019506 A1 | 2/2016 |
| WO | WO-2016057671 A1 | 4/2016 |
| WO | WO-2016102950 A1 | 6/2016 |
| WO | WO-2016102951 A1 | 6/2016 |
| WO | WO-2017148596 A1 | 9/2017 |
| WO | WO-2018011594 A1 | 1/2018 |

OTHER PUBLICATIONS

An et al. (1986) "Transformation of Tobacco, Tomato, Potato, and *Arabiodopsis thaliana* Using a Binary Ti Vector System," Plant Physiol. 81:301-305.

Ausubel et al. (1999) Short Protocols in Molecular Biology. 4th edition. pp. 7-58 to 7-60, and Chapter 18. pp. 18-1 to 18-23.

Berg et al. (1996) "Enterocolitis and colon cancer in interleukin-10-deficient mice are associated with aberrant cytokine production and CD4(+) TH1-like responses," The Journal of Clinical Investigation. 98(4):1010-1020.

Claims to be granted in European Application No. 15817513.3.

Co-pending U.S. Appl. No. 15/357,850, filed Nov. 21, 2016.

Co-pending U.S. Appl. No. 15/359,144, filed Nov. 22, 2016.

Co-pending U.S. Appl. No. 15/592,178, filed May 10, 2017.

Co-pending U.S. Appl. No. 15/631,952, filed Jun. 23, 2017.

Database UniProt [Online] Jun. 1, 2003 (Jun. 1, 2003), "subname:Full= possible pirin family protein {ECO:0000313|EMBL:AAO75294. 1};", XP002753666,retrieved from EBI accession No. UNIPROT:Q8ABC3 Database accession No. Q8ABC3.

European Communication dated Jun. 14, 2017 for EP Application No. 15817513.3.

Frame et al. (1994) "Production of fertile transgenic maize plants by silicon carbide whisker-mediated transformation," The Plant Journal. 6:941-948.

Gennaro, A.R., Remington's Pharmaceutical sciences, Mack publishing co. 1985.

Hinnen et al. (1978) "Transformation of yeast," Proc. Natl. Acad. Sci. USA. 75:1929-1933.

International Preliminary Report dated Mar. 1, 2017 for International Application No. PCT/GB2015/054113.

International Search Report dated Feb. 10, 2016 for International Application No. PCT/GB2015/054113.

International Search Report dated Mar. 7, 2016 for International Application No. PCT/GB2015/054112.

International Search report dated Mar. 15, 2003 for International Application No. PCT/GB2002/05255.

Ito et al. (1983) "Transformation of Intact Yeast Cells Treated with Alkali Cations," J. Bacteriology. 153:163-168.

Lopez-Boado, Y. S. et al., Bacterial Exposure Induces and Activates Matrilysin in Mucosal Epithelial Cells. J Cell Biol148, 1305-1315 (2000).

Mahowald et al. 'Characterizing a model human gut microbiota composed of members of its two dominant bacterial phyla.' Proceedings of the National Academy of Sciences. 2009, vol. 106, No. 14, pp. 5859-5864.

Matthes, et al., Simultaneous rapid chemical synthesis of over one hundred oligonucleotides on a microscale. Apr. 1984. EMBO Journal, 3(4): p. 801-805.

Notice of Allowance dated Mar. 30, 2011 for U.S. Appl. No. 10/285,224.

Office Action dated Jan. 11, 2005 for U.S. Appl. No. 10/285,224.

Office Action dated Jan. 26, 2009 for U.S. Appl. No. 10/275,706.

Office Action dated Feb. 18, 2010 for U.S. Appl. No. 10/285,224.

Office Action dated Mar. 13, 2013 for U.S. Appl. No. 12/760,926.

Office Action dated Mar. 26, 2007 for U.S. Appl. No. 10/275,706.

Office Action dated Apr. 4, 2008 for U.S. Appl. No. 10/285,224.

Office Action dated May 2, 2007 for U.S. Appl. No. 10/285,224.

Office Action dated May 2, 2008 for U.S. Appl. No. 10/275,706.

Office Action dated May 25, 2016 for U.S. Appl. No. 14/249,710.

Office Action dated May 26, 2009 for U.S. Appl. No. 10/285,224.

Office Action dated May 26, 2017 for U.S. Appl. No. 15/357,850.

Office Action dated May 30, 2006 for U.S. Appl. No. 10/285,224.

Office Action dated Jun. 26, 2017 for U.S. Appl. No. 15/357,936.

Office Action dated Jul. 6, 2017 for U.S. Appl. No. 15/070,605.

Office action dated Jul. 8, 2015 for U.S. Appl. No. 14/349,907.

Office Action dated Jul. 31, 2017 for U.S. Appl. No. 15/359,988.

Office Action dated Aug. 21, 2013 for U.S. Appl. No. 12/760,926.

(56) References Cited

OTHER PUBLICATIONS

Office Action dated Sep. 4, 2015 for U.S. Appl. No. 14/249,710.
Office Action dated Sep. 17, 2010 for U.S. Appl. No. 10/285,224.
Office Action dated Oct. 12, 2005 for U.S. Appl. No. 10/285,224.
Office Action dated Oct. 28, 2009 for U.S. Appl. No. 10/275,706.
Office Action dated Oct. 30, 2008 for U.S. Appl. No. 10/285,224.
Office Action dated Nov. 6, 2006 for U.S. Appl. No. 10/285,224.
Office Action dated Nov. 23, 2015 for U.S. Appl. No. 14/232,475.
Office Action dated Dec. 13, 2012 for U.S. Appl. No. 12/760,926.
Office Action dated Dec. 19, 2005 for U.S. Appl. No. 10/275,706.
Pang, et al., Crystal structure of human pirin: an iron-binding nuclear protein and transcription cofactor. Journal of Biological Chemistry, 279(2); Jan. 9, 2004:1491-1498.
Simon, et al., Peptoids: A modular approach to drug discover, Oct. 1992. PNAS, 89(20):9367-9371.
Sonnenburg, et al., Genomic and Metabolic Studies of the Impact of Probiotics on a Model Gut Symbiont and Host. PLoS Biol 4(12): e413. https://doi.org/10.1371/journal.pbio.0040413.
Srutkova, D. et al., Efficiency of PCR-based methods in discriminating *Bifidobacterium longum* ssp. longum and *Bifidobacterium longum* ssp. infantis strains of human origin.J Microbiol Methods. Oct. 2011;87(1):10-6. doi: 10.1016/j.mimet.2011.06.014. Epub Jul. 2, 2011.
Tatusova et al. (1999) "BLAST 2 Sequences, a new tool for comparing protein and nucleotide sequences," FEMS Microbial. Lett. 174(2):247-250.
Tatusova et al., Erratum to BLAST 2 Sequences, a new tool for comparing protein and nucleotide sequences, FEMS Microbiology Letters 177 (1999) 187-188.
Teng, L. J. et al., PCR Assay for Species-Specific Identification ofBacteroides thetaiotaomicron. J Clin Microbiol38, 1672-1675 (2000).
Wendler, et al., Identification of a pirin, a novel highly conserved nuclear protein. J. Biol Chem. Mar. 28, 1997; 272(13):8482-9.
Xu, et al., A genomic view of the human-Bacteroides thetaiotaomicron symbiosis. Science. Mar. 28, 2003; 299(5615):2074-6.
An et al. (1988) "Binary Vectors," Plant Molecular Biology Manual. A3:1-19.
Archer et al. (1997) "The Molecular Biology of Secreted Enzyme Production by Fungi," Critical Reviews Biotechnology. 17(4):273-306.
Beggs (1978) "Transformation of yeast by a replicating hybrid plasmid," Nature. 275:104-109.
Butcher et al. (1980) The role of tissue culture in the study of crown-gall tumorigenesis. Tissue Culture Methods for Plant Pathologists. Eds.: Ingrams, D. S.; Helgeson, J.P. pp. 203-208.
Christou (1994) "Genetic engineering of crop legumes and cereals: current status and recent advances," Agro-Food Industry Hi-Tech. pp. 17-27.
Clinical Trials for Thetanix, EU Clinical Trials Register, Date of commencement of clinical trial: Oct. 16, 2015. Available at: https://clinicaltrialsregister.eu/ctr-search/search?query=Thetanix.
Co-pending U.S. Appl. No. 15/704,245, filed Sep. 14, 2017.
Co-pending U.S. Appl. No. 15/803,721, filed Nov. 3, 2017.
Co-pending U.S. Appl. No. 15/803,723, filed Nov. 3, 2017.
Co-pending U.S. Appl. No. 15/842,635, filed Dec. 14, 2017.
Davis et al. (1971) "Genetic and Microbiological Research Technqiues," Methods Enzymol. 17A:79-143.
GT Biologics obtains FDA orphan drug designation for paediatric crohn's drug, pharmaceutical-technology.com news, Oct. 8, 2013. Available at: http://www.pharmaceutical-technology.com/news/newsgt-biologics-obtains-fda-orphan-drug-designation-for-paediatric-crohns-drug?WT.mc_id=DN_News.
Holland et al. (1990) "Secretion of Heterologous Proteins in *Escherichia coli*," Methods Enzymology. 182:132-143.
Hollenberg et al. (1997) "Production of recombinant proteins by methulotrophic yeasts," Current Opinion Biotechnology. 8(5):554-560.
Hooper at al. 'Molecular analysis of commensal host-microbial relationships in the intestine.' Science. vol. 291, No. 5505, pp. 881-884.
Kelly et al. 'Commensal anaerobic gut bacteria attenuate inflammation by regulating nuclear-cytoplasmic shuttling of PPAR-y and ReiA.' Nature Immunology. 2003, vol. 5, No. 1, pp. 104-112.
Lavallie et al. (1995) "Gene fusion expression systems in *Escherichia coli*," Current Opinion Biotechnology. 6 (5):501-506.
Meyer et al. (1992) "The use of cassava mosaic virus as a vector system for plants," Gene. 110:213-217.
Office Action dated Jan. 2, 2018 for U.S. Appl. No. 15/357,936.
Office Action dated Aug. 10, 2017 for U.S. Appl. No. 15/357,850.
Office Action dated Nov. 2, 2017 for U.S. Appl. No. 15/700,007.
Office Action dated Nov. 24, 2017 for U.S. Appl. No. 15/359,972.
Office Action dated Nov. 24, 2017 for U.S. Appl. No. 15/679,857.
Office Action dated Dec. 6, 2017 for U.S. Appl. No. 15/592,178.
Potrykus (1991) "Gene Transfer to Plants: Assessment of Published Approaches and Results," Annu. Rev. Plant Physiol. Plant Mol. Bioi. 42:205-225.
Punt et al. (2002) "Filamentous fungi as cell factories for heterologous protein production," Trends Biotechnol. 20 (5):200-206.
Trueman (1995) "Heterologous Expression in Yeast," Methods Molecular Biology. 49:341-354.
Turner (1994) "Vectors for genetic manipulation," In; Martinelli, S.D.; Kinghorn J. R.: Eds. Aspergillus: 50 years on. Progress in industrial microbiology. vol. 29. Elsevier. Amsterdam, The Netherlands. pp. 641-666.
4d Pharma Plc: "Clinical Update—RNS—London Stock Exchange", Jul. 19, 2016.
"Amedei, A. et al. Multiple sclerosis: the role of cytokines in pathogenesis and in therapies. Int J Mol Sci. Oct. 19, 2012;13(10):13438-60. doi: 10.3390/ijms131013438.".
Anonymous: "4D pharma's Blautix for Irritable Bowel Syndrome shows positive impact—pharmaceutical daily news", Dec. 13, 2016.
Arenberg, et al., Interferon-y-inducible Protein 10 (IP-10) Is an Angiostatic Factor That Inhibits Human Non-small Cell Lung Cancer (NSCLC) Tumorigenesis and Spontaneous Metastases. 1996. J. Exp.Med. 184:981-92.
Atarashi et al., Th17 Cell Induction by Adhesion of Microbes to Intestinal Epithelial Cells. Cell, vol. 163, No. 2, Oct. 8, 2015. pp. 367-380.
Atarashi, et al., Treg induction by a rationally selected mixture of Clostridia strains from the human microbiota. Supplementary Information. Nature 500, 232-236 (Aug. 8, 2013) doi:10.1038/nature12331.
Atarashi, K. et al., Treg induction by a rationally selected mixture of Clostridia strains from the human microbiota. Nature. 2013; 500(7461):232-236.
Atlas, R. Handbook of Microbiological Media, Fourth Edition. CRC Press. 2010.
Ausubel, et al. Current Protocols in Molecular Biology. 1987. Supplement 30.
Ausubel et al., Short protocols in molecular biology. Fifth edition, 2002.
Azad, M.B. et al., Probiotic supplementation during pregnancy or infancy for the prevention of asthma and wheeze: systematic review and meta-analysis BMJ 2013; 347 :f6471.
Bagge, et al., Diversity of spore-forming bacteria in cattle manure, slaughterhouse waste and samples from biogas plants. Journal of applied microbiology. 2010;109: 1549-1565.
Balato, et al., Effects of adalimumab therapy in adult subjects with moderate-to-severe psoriasis on Th17 pathway. (2014) J Eur Acad Dermatol Venereol. 28(8):1016-24.
Banfield, J. & Murphy, K.R., Non-Th2, Late-onset, non-allergic asthma. Copd & Asthma for NPs, A peer-reviewed newsletter, Aug. 2016; 14: 8 Pages.
Beaucage, et al. Deoxynucleoside phosphoramidites—A new class of key intermediates for deoxypolynucleotide synthesis. Tetrahedron Letters, vol. 22, 1981, pp. 1859-1869.
Berger, S. Gideon guide to medically important bacteria. Gideon E-book Series. 2017 edition. 4 pages.

(56) References Cited

OTHER PUBLICATIONS

Bernalier et al. *Ruminococcus hydrogenotrophicus* sp. nov., a new H2/CO2-utilizing acetogenic bacterium isolated from human feces. 1996 Arch. Microbiol. 166 (3), 176-183.
Bertram, J. et al. Establishment of a cloned line of Lewis lung carcinoma cells adapted to cell culture. (1980) Cancer let. 11:63-73.
Birdi, K.S. Handbook of Surface and Colloid Chemistry, 2nd Edition. CRC Press. 1997.
Bottacini, et al., Comparative genomics of the Bifidobacterium brevetaxon. BMC Genomics, 2014; 15:170. DOI:10.1186/1471-1471-2164-15-170.
Brand et al., Collagen-induced arthritis, 2007; Protocol 2(5):1269-1275.
Brook, I., Clinical Review: Bacteremia caused by anaerobic bacteria in children. Critical Care 6(3): 7 pages (2002).
Bry et al. A model of host-microbial interactions in an open mammalian ecosystem. Science 273(5280):1380-1383 (1996).
Busing, K. et al., Effects of oral Enterococcus faecium strain DSM 10663 NCIMB 10415 on diarrhoea patterns and performance of sucking piglets. Benef Microbes. Mar. 2015;6(1):41-4. doi: 10.3920/BM2014.0008.
"Campeau, J.L. et al., Intestinal Epithelial Cells Modulate Antigen-Presenting Cell Responses to Bacterial DNA. Infectionand Immunity. Aug. 2012; 80(8): 2632-2644.".
Caruthers, et al. New chemical methods for synthesizing polynucleotides. Nucleic Acids Symp Ser. 1980;(7):215-23.
Caspi, P.R. Experimental autoimmune uveoretinitis in the rat and mouse. Curr Protoc Immunol. May 2003;Chapter 15:Unit 15.6. doi: 10.1002/0471142735.im1506s53.
Cekanaviciute, et al., Gut bacteria from multiple sclerosis patients modulate human T cells and exacerbate symptoms in mouse models. PNAS. Jun. 30, 2017; 1-6.
Charriot, et al., Future treatment for ashtma, Eur Respir Rev 2016; 25: 77-92.
Cheluvappa, R. et al., T helper type 17 pathway suppression by appendicitis and appendectomy protects against colitis. Clin Exp Immunol. Feb. 2014;175(2):316-22. doi: 10.1111/cei.12237.
Chen, S. et al., Live combined bacillus subtilis and enterococcus faecium ameliorate murine experimental colitis by immunosuppression. International journal of inflammation. 2014(878054). 7 Pages.
Chi, W. et al., IL-23 promotes CD4+ T cells to produce IL-17 in Vogt-Koyanagi-Harada disease. J Allergy Clin Immunol. May 2007;119(5):1218-24. Epub Mar. 1, 2007.
Chi, W. et al. Upregulated IL-23 and IL-17 in Behçet patients with active uveitis. Invest Ophthalmol Vis Sci. Jul. 2008;49(7):3058-64. doi: 10.1167/iovs.07-1390.
Chiu, et al., Monocolonization of germ-free mice with bacteroides fragilis protects against dectran sulfate sodium-induced acute colitis. Biomed Research International 2014. vol. 2014. Article ID 675786. 9 Pages.
Collins, M.D., et al., *Enterococcus avium* nom. rev., comb. nov.; *E. casseliflavus* nom. rev., comb. nov.; *E. durans* nom. rev., comb. nov.; *E. gallinarum* comb. nov.; and *E. malodoratus* sp. nov. (1984) Int J Syst Evol Microbiol. 34: 220-223.
Co-pending U.S. Appl. No. 15/906,988, filed Feb. 27, 2018.
Co-pending U.S. Appl. No. 15/915,885, filed Mar. 8, 2018.
Co-pending U.S. Appl. No. 15/915,889, filed Mar. 8, 2018.
Co-pending U.S. Appl. No. 15/916,167, filed Mar. 8, 2018.
Co-pending U.S. Appl. No. 15/916,202, filed Mar. 8, 2018.
Co-pending U.S. Appl. No. 15/916,205, filed Mar. 8, 2018.
Dahya V. et al., Clostridium ramosum Osteomyelitis in an immunocompetent patient after traumatic injury, Infectious Diseases in Clinical Practice 20150312 Lippincott Williams and Wilkins USA, vol. 23, No. 2, Mar. 12, 2015, pp. 102-104, XP009193312, ISSN: 1056-9103 the whole document.
Darlington, G.J., Liver Cell Lines. (1987) Meth Enzymol. 151:19-38.
Day, J.G. et al., Cryopreservation and Freeze-Drying Protocols. Springer. 2007. 2nd edition.
Demarche, et al., Detailed analysis of sputum and systemic inflammation in asthma phenotypes: are paucigranulocytic asthmatics really non-inflammatory?, BMC Pulmonary Medicine, 2016; (16)46: 1-13.
Distrutti, et al., Gut Microbiota role in irritable bowel syndrome: New therapeutic strategies. World Journal of Gastroenterology. Feb. 21, 2016; 22(7): p. 2219-2241, XP002769875.
Divyashri et al. Probiotic attributes, antioxidant, anti-inflammatory and neuromodulatory effects of Enterococcus faecium CFR 3003: in vitro and in vivo evidence. (2015) J Med Microbiol. doi: 10.1099/jmm.0.000184.
Duncan et al. (2002) "*Roseburia intestinal* is sp. nov., a novel saccharolytic, butyrate-producing bacterium from human faeces," International Journal System Evolutionary Microbiology. 52:1615-1620.
Duncan et al. (2006) "Proposal of *Roseburia faecis* sp. nov., *Roseburia hominis* sp. nov. and *Roseburia inulinivorans* sp. nov., based on isolates from human faeces," International Journal of Systematic and Evolutionary Microbiology. vol. 56, No. Pt 10, pp. 2437-2441.
Eckburg, PB. et al., Diversity of the human intestinal microbial flora.Science. Jun. 10, 2005;308(5728):1635-8. Epub Apr. 14, 2005.
Embl sequence AAO75294.1 (2003)—provided within the Office Action dated Feb. 16, 2018 in U.S. Appl. No. 15/631,952. 2 Pages.
Fabro, A. et al., The Th17 pathway in the peripheral lung microenvironment interacts with expression of collagen V in the late state of experimental pulmonary fibrosis. (2015) Immunobiology. 220(1):124-35.
Faghih, Z. et a., IL-17 and IL-4 Producing CD8+ T Cells in Tumor Draining Lymph Nodes of Breast Cancer Patients: Positive Association with Tumor Progression. (2013). Iranian Journal of Immunology. 10(4):193-204.
Fahy, J.V. Eosinophilic and neutrophilic inflammation in asthma: insights from clinical studies. Proc Am Thorac Soc. May 1, 2009;6(3):256-9. doi: 10.1513/pats.200808-087RM.
Farooq, P.D. et al., Pseudomembranous colitis, Disease-A-Month 2015 Mosby Inc. USA, vol. 61, No. 5, May 1, 2015, pp. 181-206, XP009193313, ISSN: 0011-5029 p. 195.
FDA Orphan Drug Designations. Total Orphan Drugs website. Aug. 2014. Available at http://www.orphan-drugs.org/2014/09/01/fda-orphandrug- designations-august-2014. Accessed on Apr. 13, 2016.
Fenner, et al., *Bacteroides massiliensis* sp. nov., isolated from blood culture of a newborn. International Journal of systematic and evolutionary microbiology, 2005. 55: 1335-1337.
Frank, D. et al., Molecular-phylogenetic characterization of microbial community imbalances in human inflammatory bowel diseases. 2007. PNAS. 104(34):13780-5.
Frick, et al., Identification of commensal bacterial strains that modulate Yersinia enterocolitica and Dextran sodium sulfate-induced inflammatory responses: implications for the development of probiotics. Infection and immunity, Jul. 2007;75(7):3490-3497.
GB Exam and search report dated Aug. 30, 2016 for GB Application No. 1520638.6.
GB Search and Exam report dated Mar. 31, 2016 for GB application 1510469.8.
GB Search and Exam report dated Mar. 31, 2016 for GB application 1510470.6.
GB Search and Exam report dated Apr. 15, 2016 for GB application 1510467.2.
GB Search and Exam report dated Apr. 20, 2016 for GB application 1510466.4.
GB Search and Exam report dated Apr. 20, 2016 for GB application 1510468.0.
GB Search and Exam report dated Aug. 30, 2016 for GB application No. 1520631.1.
GB Search and Exam report dated Nov. 17, 2016 for GB application 1520502.4.
GB Search and Exam report dated Sep. 13, 2016 for GB application 1520497.7.
Gennaro, A.R. "Quality Assurance and Control," from Remington: The Science and Practice of Pharmacy, 2000, Lippincott Williams & Wilkins, 20th ed., pp. 980-983.

(56) References Cited

OTHER PUBLICATIONS

Ghadimi, D. et al., Epigenetic imprinting by commensal probiotics inhibits the IL-23/IL-17 axis in an in vitro model of the intestinal mucosal immune system. JLB. 2012;92(4):895-911.
Goldin, B.R. et al., Clinical indications for probiotics: an overview. Clin Infect Dis. Feb. 1, 2008;46 Suppl 2:S96-100; discussion S144-51. doi: 10.1086/523333.
Greenspan et al., Defining epitopes: Its not as easy as it seems. Nature Biotechnology 7: 936-937, 1999.
Guide for the care and use of laboratory animals: 8th edition. The national academic press; 2011.
Haabeth et al. A model for cancer-suppressive inflammation. (2012) Oncolmmunology 1(1):1146-1152.
Hammerich, L. et al., Interleukins in chronic liver disease: lessons learned from experimental mouse models. (2014) Clin Exp Gastroenterol. 7:297-306.
Handbook of Experimental Immunology, vols. I IV (D.M. Weir and C.C. Blackwell, eds, 1986, Blackwell Scientific Publications).
Holdeman, et al., *Eubacterium contortum* (Prevot) comb. nov.: Emendation of description and designation of the type strain. International journal of systematic bacteriology. Oct. 1971;21(4):304-306.
Horn, et al., Synthesis of Oligonucleotides on Cellulose. Part II: Design and Synthetic Strategy to the Synthesis of 22 Oligodeoxynucleotides Coding for Gastric Inhibitory Polypeptide (GIP). 1980. Nuc Acids Res Symp Ser 225-232.
Horwell, et al., The 'peptoid' approach to the design of non-peptide, small molecule agonists and antagonists of neuropeptides. 1995. Trends Biotechnol. 13(4):132-134.
Hougee, et al., Oral treatment with probiotics reduces allergic symptoms in ovalbumin-sensitized mice:a bacterial strain comparative study. Int Arch Allergy Immunol. 2010; 151:107-117.
International Search Report dated Jan. 27, 2017 for International Application No. PCT/GB2016/053622.
International Search Report dated Feb. 17, 2017 for International Application No. PCT/GB2016/053676.
International Search Report dated Aug. 26, 2016 for International application No. PCT/GB2016/051774.
International Search Report dated Aug. 26, 2016 for International application No. PCT/GB2016/051776.
International Search Report dated Sep. 6, 2016 for International application No. PCT/GB2016/051768.
International Search Report dated Sep. 6, 2016 for International application No. PCT/GB2016/051773.
International Search Report dated Sep. 6, 2016for International application No. PCT/GB2016/051770.
International Search Report dated Feb. 2, 2017 for International application No. PCT/GB2016/053620.
International Search Report dated Mar. 6, 2017 for International Application No. PCT/GB2016/053677.
International search report with written opinion dated Feb. 26, 2018 for PCT/GB2017/053722.
International search report with written opinion dated Oct. 16, 2017 for PCT/GB2017/052076.
Ispirli, H. et al., Characterization of functional properties of Enterococcus faecium strains isolated from human gut.Can. J. Microbiol. 61: 861-870 (2015) dx.doi.org/10.1139/cjm-2015-0446.
Jawad, S. et al., Elevated serum levels of interleukin-17A in uveitis patients. Ocul Immunol Inflamm. Dec. 2013;21(6):434-9. doi: 10.3109/09273948.2013.815786. Epub Aug. 19, 2013.
Jiao et al., Blockade of Notch Signaling Ameliorates Murine Collagen-Induced Arthritis via Suppressing Th1 and Th17 Cell Responses. 2014; Pathology, 184(4):1085-1093.
Kailasapathy, K. Microencapsulation of Probiotic Bacteria:Technology and Potential Applications. Curr. Issues Intest. Microbiol. (2002) 3: 39-48.
Kanauchi, et al., Eubacterium limosum ameliorates experimental colitis and metabolite of microbe attenuates colonic inflammatory action with increase of mucosal integrity introduction, China World J Gastroenterol February, Jan. 1, 2006. pp. 1071-1077.
Kanauchi, et al., Eubacterium limosum (probiotic) and its metabolites showed anti-inflammatory effects and increased mucosal barrier function in colitis. S1912.
Kang, S. et al., Dysbiosis of fecal microbiota in Crohn's disease patients as revealed by a custom phylogenetic microarray.Inflamm Bowel Dis. Dec. 2010;16(12):2034-42. doi: 10.1002/ibd.21319.
Karaffova, et al., Interaction of TGF-B4 and IL-17 with IgA secretion in the intestine of chickens fed with E. faecium AL41 and challenged with S. Enteritidis. Research in Veterinary science. 2015:75-79.
Karin, M. Nuclear factor-kappaB in cancer development and progression. Nature. May 25, 2006;441(7092):431-6.
Kirsty Minton: Mucosal immunology: The ins and outs of gut inflammation, The journal of immunology, 4(2), Feb. 1, 2004: pp. 81-81, XP055252701.
Kitahara, M. et al., *Bacteroides plebeius* sp. nov. and *Bacteroides coprocola* sp. nov., isolated from human faeces. International journal of systematic and evolutionary microbiology. 2005; 55: 2143-2147.
Koenders, M.I. et al., Interleukin-17 Acts Independently of TNF-a under Arthritic Conditions. (2006) J. Immunol. 176:6262-6269.
Kogyo, S. Lactic Acid Bacteria, Intestinal Flora ad Health II; Physiological effects of heat-treated lactococcus "EF-2001" and application to food. Mar. 30, 2001 vol. 44, No. 6, pp. 35-39.
Kverka, M. et al., Oral administration of Parabacteroides distasonis antigens attenuates experimental murine colitis through modulation of immunity and microbiota composition. Clinical & Experimental Immunology. 2010; 163:250-259.
Laukova, A. et al. Benefits of Combinative Application of Probiotic, Enterocin M-Producing Strain Enterococcus Faecium AL41 and Eleutherococcus Senticosus in Rabbits. Folia Microbiol (Praha) 61 (2), 169-177. Sep. 9, 2015.
Lee, et al. Intestinal microbiota in pathophysiology and management of irritable bowel syndrome . 2014. World J Gastroenterol. 20(27): 8886-8897.
Lejeune, FJ. et al., Efficiency of Recombinant Human TNF in Human Cancer Therapy. (2006) Cancer Immun. 6:6.
Leslie, et al., Trehalose and sucrose protect both membranes and proteins in intact bacteria during drying. (1995) Appl. Environ. Microbiol. 61, 3592-3597.
Liu et al. Reclassification of Clostridium coccoides, Ruminococcus hansenii, Ruminococcus hydrogenotrophicus, Ruminococcus luti, Ruminococcus productus and Ruminococcus schinkii as *Blautia coccoides* gen. nov., comb. nov., *Blautia hansenii* comb. nov., *Blautia hydrogenotrophica* comb. nov., *Blautia luti* comb. nov., *Blautia producta* comb. nov., *Blautia schinkii* comb. nov. and description of *Blautia wexlerae* sp. nov., isolated from human faeces. 2008. Int J Syst Evol Microbiol 58,1896-1902.
Lodemann, U. et al., Effects of the Probiotic enterococcus faecium and pathogenic *Escherichia coli* strains in a pig and human epithelial intestinal cell model. Hindawi publishing corporation scientifica. 2015(235184) 10 pages.
Lopetuso et al. Commensal Clostridia: leading players in the maintenance of gut homeostasis. 2013. Gut Pathogens, 5: 23.
Luger, D. and Caspi, R.R., New perspectives on effector mechanisms in uveitis. (2008) Semin. Immunopathol. 30(2): 134-143.
Lyons, et al., Bacterial strain-specific induction of Foxp3 T regulatory cells is protective in murine allergy models. Clinical & Experimental Allergy. 2010; 40:811-819.
Machiels, K. A decrease of the butyrate-producing species Roseburia hominis and Faecalibacterium prausnitzii defines dysbiosis in patients with ulcerative colitis.Gut. Aug. 2014;63(8):1275-83. doi: 10.1136/gutjnl-2013-304833. Epub Sep. 10, 2013.
MacPherson, AJ. et al., IgA responses in the intestinal mucosa against pathogenic and non-pathogenic microorganisms. Oct. 2001. 3(12). 1021-1035.
MacPherson, AJ., et al., The functions of mucosal T cells in containing the indigenous commensal flora of the intestine.Cell Mol Life Sci. Dec. 2002;59(12):2088-96.
MacSharry et al., Immunomodulatory effects of feeding with bifidobacterium longum on allergen-induced lung inflammation in the mouse. Pulmonary pharmacology & Therapeutics. 2012; 25:325-334.

(56) References Cited

OTHER PUBLICATIONS

Maintaining Cultures for Biotechnology and Industry (1996) Jennie C. Hunter-Cevera, Academic Press.
Manni et al., A tale of two cytokines: IL-17 and IL-22 in asthma and infection. Expert Rev Respir Med. Feb. 2014 ; 8(1): 25-42. doi:10.1586/17476348.2014.854167.
Mansour et al. Isolation of Enterococcus faecium NM113, Enterococcus faecium NM213 and Lactobacillus casei NM512 as novel probiotics with immunomodulatory properties. (2014) Microbiol Immunol. 58(10):559-69.
Masco, L., et al., Identification of Bifidobacterium Species Using rep-PCR Fingerprinting. Systematic and Applied Microbiology 26(4):557-63 • Dec. 2003.
Maya, J.R. et al., Emerging Therapies for Noninfectious Uveitis: What May Be Coming to the Clinics. (2014) J. Ophthalmology. 310329.
Mazmanian et al. 'An immunomodulatory molecule of symbiotic bacteria directs maturation of the host immune system.' Cell. 2005, vol. 122, No. 1, pp. 107-118.
Miossec, P. et al. Targeting IL-17 and TH17 cells in chronic inflammation. Nat Rev Drug Discov. Oct. 2012;11(10):763-76. doi: 10.1038/nrd3794.
Mitropoulou, G. et al. Immobilization Technologies in Probiotic Food Production. (2013) Journal Nutr Metab. (2013) 716861.
Miyake, T. et al., Phylogenetic Analysis of the Genus Bifidobacterium and Related Genera Based on 16S rDNA Sequences. Microbiol. Immunol. 1998; 42(10):661-667.
Miyamoto-Shinohara et al. Survival of freeze-dried bacteria. J Gen Appl Microbiol 54(1):9-24 (2008).
Miyauchi, E., Control of multiple sclerosis by gut microbiota. Journal of clinical and experimental medicine. 2015. vol. 253 No. 5.2, pp. 445-450.
Molecular Biology Techniques: An Intensive Laboratory Course, (Ream et al., eds., 1998, Academic Press).
Monteleone, I. et al., Th17-related cytokines: new players in the control of chronic intestinal inflammation. (2011) BMC Medicine. 2011, 9:122.
Mucientes, A. et al., Specific association of IL17A genetic variants with panuveitis. (2015) Br J Ophthalmol. 99(4):566-70.
Mukai et al., SH3BP2 Gain-Of-Function Mutation Exacerbates Inflammation and Bone Loss in a Murine Collagen-Induced Arthritis Model, 2014 PLoS One 9(8): e105518.
Narushima, et al., Characterization of the 17 strains of regulatory T cell-inducing human-derived Clostridia. Gut Microbes Mar. 18, 2014; 5:3, 333-339.
Neish, A. S. et al., Prokaryotic Regulation of Epithelial Responses by Inhibition of IκB-αUbiquitination. Science 289, 1560 (2000).
Notice of allowance dated Sep. 1, 2017 for U.S. Appl. No. 15/357,850.
Notice of Allowance dated Nov. 22, 2017 for U.S. Appl. No. 15/359,988.
Nuala Moran: 'Microbial wealth', chemistry and industry, 78(6), Jun. 1, 2014, pp. 20-23, XP055252922.
Numasaki, M. et al., IL-17 Enhances the Net Angiogenic Activity and In Vivo Growth of Human Non-Small Cell Lung Cancer in SCID Mice through Promoting CXCR-2-Dependent Angiogenesis. (2005) J. Immunol. 175: 6177-6189.
Numasaki, M. et al., Interleukin-17 promotes angiogenesis and tumor growth. Blood. Apr. 1, 2003;101(7):2620-7. Epub Oct. 31, 2002.
Oladipo, et al., Bioprotective potential of bacteriocinogenic enterococcus gallinarum strains isolated from some Nigerian fermented foods, and of their bacteriocins. Polish Journal of Microbiology. 2014; 63(4): 415-422.
Overstreet et al. 'Dysbiosis Characterized by Reduced Abundance of Roseburia is Associated With Increased Severity of Colitis in IL-10-/-Mice'. Gastroenterology. 2011, vol. 140, No. 5, Suppl. 1, pp. S-696.
Pace et al. Macrophage activiation: Priming activity from a T-cell hybridoma is attributable to interferon. (1983) PNAS. 80:3782-6.
Parabacteroides distasonis (Eggerth and Gagnon) Sakamoto and Benno (ATCC 8503). Sep. 19, 2017. 2 Pages.
Park, S.K. et al., Blautia stercoris sp. nov., isolated from human faeces. International journal of systematic and evolutionary microbiology. 2012; 62(4): 776-779.
Patel., R. et al., Determination of 16S rRNA sequences of enterococci and application to species identification of nonmotile enterococcus gallinarum isolates. Journal of clinical microbiology, 1998; 36(11):3399-3407.
PCR (Introduction to Biotechniques Series), 2nd ed. (Newton & Graham eds., 1997, Springer Verlag).
PCT/EP2017/025038 Written Opinion of the International Preliminary Examining Authority dated Jan. 1, 2018.
Pearson, WR. An introduction to sequence similarity ("Homology") searching. Current protocols in bioinformatics/editoral board, Andreas D Baxevanis. 2013; 0 3:10.1002/0471250953.bi0301s42. doi:10.1002/0471250953.bi0301s42.
Robinson, et al. Inside information—The unique features of visceral sensation. 2008. Mol Interv, 8(5): 242-253.
Rockwell, S.C. et al., Characteristics of a Serially Transplanted Mouse Mammary Tumor and Its Tissue-Culture-Adapted Derivative. (1972) J Natl Cancer Inst. 49:735-49.
Rudinger et al., Characteristics of the amino acids as components of a peptide hormone sequence. Peptide Hormones. Biol. Council. Jun. 1976; 10 Pages.
Sagar, et al., Bifidobacterium breve and lactobacillus rhamnosus treatment is as effective as budesonide at reducing inflammation in a murine model for chronic asthma. Respiratory Research. 2014; 15(46):1-17.
Saiki, et al., Primer-directed enzymatic amplification of DNA with a thermostable DNA polymerase. 1988. Science, 239. pp. 487-491.
Sakamoto, M. et al., Reclassification of Bacteroides distasonis, Bacteroides goldsteinii and Bacteroides merdae as Parabacteroides distasonis gen. nov., comb. nov., Parabacteroides goldsteinii comb. nov. and Parabacteroides merdae comb. nov. International journal of systematic and evolutionary microbiology. 2006; 56: 1599-1605.
Salix Pharmaceuticals, Inc. FDA Highlights of Prescribing Information—XIFAXAN (rifaximin tablet). Revised Nov. 2015.
Sambrook, J.F. et al., Molecular Cloning: A Laboratory Manual, 3rd ed. Cold spring harbor laboratory press. 2001.
Scanlan PD., et al., Culture-independent analyses of temporal variation of the dominant fecal microbiota and targeted bacterial subgroups in Crohn's disease. J Clin Microbiol. Nov. 2006;44(11):3980-8. Epub Sep. 20, 2006.
Scher et al., Expansion of intestinal Prevotella copri correlates with enhanced susceptibility to arthritis. 2013; eLIFE 2, e01202, 20 Pages.
Schieck, M. et al., Genetic variation in TH17 pathway genes, childhood asthma, and total serum IgE levels.(2014) J Allergy Clin Immunol. 133(3):888-91.
Schleifer, K.H. et al., Transfer of Streptococcus faecalis and Streptococcus faecium to the Genus Enterococcus nom. rev. as Enterococcus faecalis comb. nov. and Enterococcus faecium comb. nov. Int J Syst Evol Microbiol, Jan. 1984 34: 31-34, doi:10.1099/00207713-34-1-31 .
Schmitz, S. et al., A prospective, randomized, blinded, placebo-controlled pilot study on the effect of Enterococcus faecium on clinical activity and intestinal gene expression in canine food-responsive chronic enteropathy. J Vet Intern Med. Mar.-Apr. 2015;29(2):533-43. doi: 10.1111/jvim.12563. Epub Mar. 16, 2015.
Schouten, et al., Cow milk allergy symptoms are reduced in mice fed dietary synbiotics during oral sensitization with whey. Nutritional Immunology. 2015; 139(7):1390-403.
Schwiertz, et al., Quantification of Different Eubacterium spp. in Human Fecal Samples with Species-Specific 16S rRNA-Targeted Oligonucleotide Probes. Applied and environmental biology, vol. 66, No. 1, Jan. 1, 2000; pp. 375-382.
Severijnen, et al., Chronic Arthritis Induced in Rats by Cell Wall Fragments of Eubacterium Species from the Human Intestinal Flora. Infection and Immunity, Feb. 1990; 58(2): p. 523-528.
Sgadari, C. et al., Interferon-inducible protein-10 identified as a mediator of tumor necrosis in vivo. (1996) PNAS. 93:13791-6.

(56) References Cited

OTHER PUBLICATIONS

Sgadari et al. Mig, the Monokine Induced by Interferon-g, Promotes Tumor Necrosis in Vivo. (1997) Blood. 89:2635-43.

Shabgah, A.G. et al., Interleukin-17 in human inflammatory diseases. Postepy Dermatol Alergol. Aug. 2014; 31(4): 256-261.

Simpson-Herren, L. et al., Kinetic parameters and growth curves for experimental tumor systems. Cancer Chemother Rep. Jun. 1970;54(3):143-74.

Sisson, G. et al., Randomised clinical trial: a liquid multi-strain probiotic vs. placebo in the irritable bowel syndrome—a 12 week double-blind study. Aliment Pharmacol Ther. 2014; 40: 51-62.

Sivieri, K. et al., Probiotic enterococcus faecium CRL 183 inhibit chemically induced colon cancer in male wistar rats. Eur Food Res Technol. 2008; 228:231-237.

Skolnick, et al. From genes to protein structure and function: novel applications of computational approaches in the genomic era. Trends Biotechnol. Jan. 2000;18(1):34-9. Review.

Smith, T.F. et al., Comparison of biosequences. (1981) Adv. Appl. Math. 2: 482-489.

Song et al., Impact of Schistosoma japonicum Infection on Collagen-Induced Arthritis in DBA/1 Mice: A Murine Model of Human Rheumatoid Arthritis. 2011; PLoS One 6, e23453, 10 pages.

Spor, A. et al., Unravelling the effects of the environment and host genotype on the gut microbiome. Nat Rev Microbiol. Apr. 2011;9(4):279-90. doi: 10.1038/nrmicro2540.

Stanton et al. (1983) "*Roseburia cecicola* gen. nov., sp. nov., a Motile, Obligately Anaerobic Bacterium from a Mouse Cecum," Int. J. Syst. Bacterial. 33:618-627.

Stoll et al., Altered microbiota associated with abnormal humoral immune responses to commensal organisms in enthesitis-related arthritis, 2014; Arthritis Res Ther. 16:486.

Strickertsson, J.A. et al., Enterococcus faecalis Infection and Reactive Oxygen Species Down-Regulates the miR-17-92 Cluster in Gastric Adenocarcinoma Cell Culture. Genes 2014, 5(3), 726-738.

Strobel, H.J. Basic laboratory culture methods for anaerobic bacteria. Methods Mol Biol. 2009;581:247-61. doi: 10.1007/978-1-60761-214-8_16.

Sun, D. et al., The role of Th17-associated cytokines in the pathogenesis of experimental autoimmune uveitis (EAU). (2015) Cytokine. 74(1):76-80.

Tamanai-Shacoori, et al., *Roseburia* spp.: a marker of health?. Future Microbiology Review 12(2), 157-170 (2017).

Tanaka, K. and Watanabe, K., In Vitro tebipenem activity against anaerobic bacteria. Japanese Journal of Chemotherapy. Mar. 2009. vol. 57 S-1.

Tap et al. Towards the human intestinal microbiota phylogenetic core. 2009. Environ Microbiol, 11(10):2574-84.

Tesmer, L.A. et al., Th17 cells in human disease. Immunol Rev. 2008;223:87-113.

Toomer, O. et al., Maternal and postnatal dietary probiotic supplementation enhances splenic regulatory T helper cell population and reduces peanut allergen-induced hypersensitivity responses in mice. Immunobiology. 209; 2014: 661-670.

Tsukinowa, et al., Fecal microbiota of a dugong (Dugong dugong) in captivity at Toba Aquarium. J. Gen. Appl. Microbiol., 54, 25-38 (2008).

Udayappan, et al., Oral treatment with Eubacterium hallii improves insulin sensitivity in db/db mice. Npj Biofilms and microbiomes, vol. 2, Jul. 6, 2016; p. 16009.

Udayappan et al., PS4-5. Administration of Eubacterium hallii improves insulin sensitivity and degree of liversteatosis in male db/db mice. Nederlands tijdschrift voor diabetologie, vol. 11, No. 4, Nov. 23, 2013.pp. 145.

U.S. Appl. No. 15/359,988 Notice of Allowance dated Mar. 2, 2018.

U.S. Appl. No. 15/359,988 Notice of Allowance dated Mar. 16, 2018.

U.S. Appl. No. 15/631,952 Office Action dated Feb. 16, 2018.

U.S. Appl. No. 15/679,857 Office Action dated Feb. 14, 2018.

U.S. Appl. No. 15/803,723 Notice of Allowance dated Feb. 13, 2018.

Van De Veerdonk, et al., The Anti-CD20 antibody rituximab reduces the Th17 cell response. Arthritis & Rheumatism. Jun. 2011; 63(6):1507-1516.

Vetrovsky, T. and Baldrian, P., The variability of the 16S rRNA gene in bacterial genomes and its consequences for bacterial community analyses. Plos One. Feb. 2013; 8(2): e57923.

Workman et al. Guidelines for the welfare and use of animals in cancer research (2010) Br. J. Cancer. 102:1555-77.

Wunderlich, P.F. et al., Double-blind report on the efficacy of lactic acid-producing enterococcus SF68 in the prevention of antibiotic-associated diarrhoea and in the treatment of acute diarrhoea. The journal of international medical research. 1989; 17: 333-338.

Xu, et al., the endogenous hydrogen sulfide producing enzyme cystathionine-i synthase contributes to visceral hypersensitivity in a rat model of irritable bowel syndrome. Molecular Pain, Biomed central, London, GB. Aug. 6, 2009; 5(1):p. 44.

Xu, J. et al., "Message from a human gut symbiont: sensitivity is a prerequisite for sharing", Trends in microbiology, 12(1), Jan. 1, 2004: pp. 21-28, XP055253932.

Yang, J. et al., Targeting Th17 cells in autoimmune diseases. Trends Pharmacol Sci. Oct. 2014;35(10):493-500. doi: 10.1016/j.tips.2014.07.006. Epub Aug. 14, 2014.

Ye, X. et al., The Role of IL-23/Th17 Pathway in Patients with Primary Immune Thrombocytopenia. (2015) PLoS One. 10(1):e0117704.

Yin, X. et al., Combined effect of five single nucleotide polymorphisms related to IL23/Th17 pathway in the risk of psoriasis. Immunogenetics. Mar. 2014;66(3):215-8. doi: 10.1007/s00251-013-0756-z. Epub Jan. 14, 2014.

Yurdusev, N. et al., Antagonistic Effect Exerted by Three Strictly Anaerobic Strains Against Various Strains of Clostridium Perfringens in Gnotobiotic Rodent Intestines. Can J Microbiol 33, 226-231 (1987).

Yurdusev, N. et al., InfectInunun 57,724-731 (1989).

Yutin, N. and Galperin, M.Y., A genomic update on clostridial phylogeny:Gram-negative spore formers and other misplaced clostridia. Environmental microbiology. 20136; 15(10): 2631-2641.

Zhang, B. et al., Oral administration of enterococcus faecalis FK-23 suppresses Th17 cell development and attenuates allergic airway responses in mice. International journal of molecular medicine. 2012; 30:248-254.

Zhang, B. et al., The Prevalence of Th17 Cells in Patients With Gastric Cancer. 2008. Biochem Biophys Res Commun 374 (3), 533-537.

Zhang, et al., The Activation of NF-κb in Infiltrated Mononuclear Cells Negatively Correlates with Treg Cell Frequency in Oral Lichen Planus. Inflammation. Aug. 2015;38(4):1683-9. doi: 10.1007/s10753-015-0145-x.

Zheng, B. et al., Bifidobacteriu breve attenuates murine dextran sodium sulfate-induced colitis and increases regulatory T cell responses. PLOS one. May 2014; 9(5).

Zhongyuan, T. et al., The inflammation regulation effects of enterococcus faecium HDRsEf1 on human enterocyte-like HT-29 cells. Animal cells and systems. Mar. 2016;20(2):70-76.

Zhou et al. Central and peripherial hypersensitivity in the irritable bowel syndrome. 2010. Pain. 148(3): 454-461.

Zhu, S. and Qian, Y., IL-17/IL-17 receptor system in autoimmune disease: mechanisms and therapeutic potential. Clinical Science (2012) 122, 487-511.

Zitomersky, N. et al., Characterization of Adherent Bacteroidales from Intestinal Biopsies of Children and Young Adults with Inflammatory Bowel Disease. PLOS one. 2013; 8(6).

Zitvogel, et al., Type I interferons in anticancer immunity. Nature Reviews. Jul. 2015:405-414.

U.S. Appl. No. 10/046,015, filed Aug. 14, 2018, Mulder, Imke Elisabeth et al.

U.S. Appl. No. 10/058,574, filed Aug. 28, 2018, Grant, George et al.

Christmann, et al., Human seroreactivity to gut microbiota antigens. J Allergy Clin Immunol 136(5):1378-1386; available online May 23, 2015.

(56) References Cited

OTHER PUBLICATIONS

Colin, et al., GIC-1001, A Clinical Stage, Orally Administered Colonic Analgesic Drug Proposed As a Cost-Effective Alternative to I.V. Sedation Used in Colonoscopy. Canadian Digestive Diseases Week, 2014; 2 pages.
Co-pending U.S. Appl. No. 16/022,207, filed Jun. 28, 2018.
Co-pending U.S. Appl. No. 16/022,256, filed Jun. 28, 2018.
Co-pending U.S. Appl. No. 16/022,484, filed Jun. 28, 2018.
Co-pending U.S. Appl. No. 16/022,577, filed Jun. 28, 2018.
Co-pending U.S. Appl. No. 16/031,024, filed Jul. 10, 2018.
Co-pending U.S. Appl. No. 16/040,356, filed Jul. 19, 2018.
Distrutti, et al., 5-Amino-2-hydroxybenzoic Acid 4-(5-Thioxo-5H-[1,2]dithiol-3yl)-phenyl Ester (ATB-429), a Hydrogen Sulfide-Releasing Derivative of Mesalamine, Exerts Antinociceptive Effects in a Model of Postinflammatory Hypersensitivity. The Journal of pharmacology and experimental therapeutics, 2006;319(1):447-458.
Farmer, et al., Gut pain & visceral hypersensitivity. British journal of pain, 2013;7(1):39-47.
Sun, et al., Exploring gut microbes in human health and disease: Pushing the envelope. Genes Dis. Dec. 2014; 1(2):132-139.doi:10.1016/j.gendis.2014.08.001.
U.S. Appl. No. 15/631,952 Office Action dated Jul. 19, 2018.
U.S. Appl. No. 15/679,857 Office Action dated Aug. 6, 2018.
U.S. Appl. No. 15/842,635 Office Action dated Aug. 27, 2018.
Van Tilburg, M. Can we treat visceral hypersensitivity in functional abdominal pain? Lancet Gastroenterolhepatol, 2017; 2 Pages.
Co-pending U.S. Appl. No. 15/969,543, filed May 2, 2018.
Ishikawa, et al., Effect of bifidobacteria to suppress Th17, Food Science and technology institute, 2008, 5 Pages.
U.S. Appl. No. 15/700,007 Office Action dated Jun. 1, 2018.
U.S. Appl. No. 15/357,936 Notice of Allowance dated Apr. 18, 2018.
U.S. Appl. No. 15/592,178 Notice of Allowance dated Apr. 12, 2018.
U.S. Appl. No. 15/916,202 Notice of Allowance dated Jun. 11, 2018.
U.S. Appl. No. 15/359,144 Office Action dated Apr. 10, 2018.
U.S. Appl. No. 15/359,972 Office Action dated Apr. 4, 2018.
U.S. Appl. No. 15/673,270 Office Action dated Apr. 10, 2018.
Van De Bogert, et al., Immunomodulatory properties of streptococcus and veillonella isolates from the human small intestine microbiota, PLOS One, Dec. 2014: 1-20, DOI:10.1371/journal.pone.0114277.

* cited by examiner

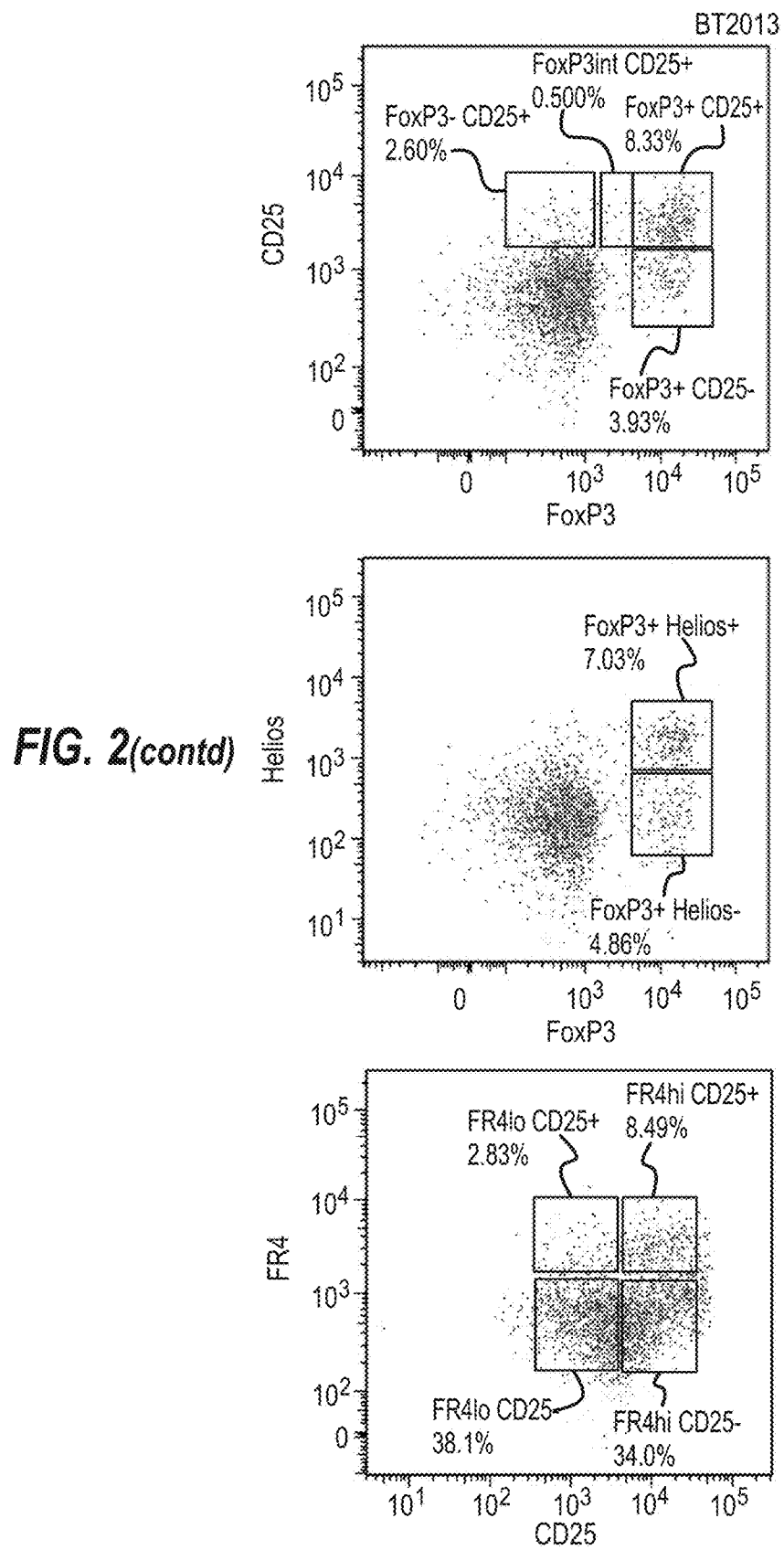
FIG. 2(contd)

| control vs BT2013 | * | P<0.05 |
| --- | --- | --- |
| control vs BT E1 | * | P<0.05 |
| control vs BTE2 | ** | P<0.01 |
| control vs DSS | *** | P<0.001 |
| BT2013 vs BTE1 | ns | P>0.05 |
| BT2013 vs BTE2 | ns | P>0.05 |
| BT2013 vs DSS | *** | P<0.001 |
| BT E1 vs BTE2 | ns | P>0.05 |
| BT E1 vs DSS | *** | P<0.001 |
| BTE2 vs DSS | *** | P<0.001 |

| | | |
|---|---|---|
| control vs BT2013 | ** | P<0.01 |
| control vs BT E1 | * | P<0.05 |
| control vs BTE2 | * | P<0.05 |
| control vs DSS | *** | P<0.001 |
| BT2013 vs BTE1 | ns | P>0.05 |
| BT2013 vs BTE2 | ns | P>0.05 |
| BT2013 vs DSS | ** | P<0.01 |
| BT E1 vs BTE2 | ns | P>0.05 |
| BT E1 vs DSS | ** | P<0.01 |
| BTE2 vs DSS | ** | P<0.01 |

COMPOSITION OF BACTEROIDES THETAIOTAOMICRON FOR IMMUNE MODULATION

CROSS-REFERENCE

This application is a continuation of International Application No. PCT/GB2015/054112, filed Dec. 22, 2015, which claims the benefit of Great Britain application No. 1423084.1, filed Dec. 23, 2014, which are hereby incorporated by reference in their entirety.

SEQUENCE LISTING

The instant application contains a Sequence Listing which has been submitted electronically in ASCII format and is hereby incorporated by reference in its entirety. Said ASCII copy, created on May 31, 2017, is named BT2013 sequence listings SEQ ID 1.txt and is 8,310,124 bytes in size.

FIELD OF THE INVENTION

The present invention relates to microorganisms that are able to positively modulate inflammatory disorders and which may be used in therapy or preventative medicine.

BACKGROUND OF THE INVENTION

*Bacteroides thetaiotaomicron* has potent anti-inflammatory effects in vitro and in vivo (Kelly et al. Commensal anaerobic gut bacteria attenuate inflammation by regulating nuclear-cytoplasmic shuttling of PPAR-gamma and RelA. Nat Immunol. 2004 January; 5(1):104-12). It modulates molecular signalling pathways of NF-κB (Kelly et al, Commensal anaerobic gut bacteria attenuate inflammation by regulating nuclear-cytoplasmic shuttling of PPAR-gamma and RelA. Nat Immunol. 2004 January; 5(1):104-12). In particular, it stops binding of the active component (RelA) of NF-κB to key genes in the nucleus, thereby preventing the activation of pro-inflammatory pathways (Kelly et al, Supra 2004). The full genome of *B. thetaiotaomicron* was sequenced and annotated by the Gordon Group (Washington University School of Medicine, USA) in 2003 [Xu et al, A genomic view of the human-*Bacteroides thetaiotaomicron* symbiosis. Science. 2003 Mar. 28; 299(5615):2074-6].

SUMMARY OF THE INVENTION

The present invention is based on the discovery of a strain of *Bacteroides thetaiotaomicron* (BT) that has surprising efficacy against inflammatory disorders. Accordingly the strain of BT is useful as a therapeutic or in preventative medicine against inflammatory disorders and/or autoimmune disorders and/or allergic disorders.

According to a first aspect of the invention, there is a *Bacteroides thetaiotaomicron* deposited as NCIMB Accession Number 42341, or a derivative thereof.

According to a second aspect of the invention, there is a nutritional supplement comprising a *Bacteroides thetaiotaomicron* as defined in claim 1, and a nutritionally acceptable excipient, carrier or diluent.

According to a third aspect of the invention, there is a feedstuff, food product, dietary supplement, or food additive comprising a *Bacteroides thetaiotaomicron* as defined in claim 1.

According to a fourth aspect of the invention, a *Bacteroides thetaiotaomicron* as defined in claim 1, a composition as defined in claim 2 or 3, a pharmaceutical composition as defined in claim 4 or 5, a nutritional supplement as defined in claim 6 or 7 or a feedstuff, a food product, a dietary supplement, or a food additive as defined in claim 8 or 9, for use in modulating the inflammation of a tissue or an organ in a subject.

According to a fifth aspect of the invention, a *Bacteroides thetaiotaomicron* as defined in claim 1, a composition as defined in claim 2 or 3, a pharmaceutical composition as defined in claim 4 or 5, a nutritional supplement as defined in claim 6 or 7 or a feedstuff, a food product, a dietary supplement, or a food additive as defined in claim 8 or 9, for use in the treatment and/or prevention of a disorder in a subject; wherein said disorder is an inflammatory disorder and/or an autoimmune disorder.

According to a sixth aspect of the invention, a *Bacteroides thetaiotaomicron* as defined in claim 1, a composition as defined in claim 2 or 3, a pharmaceutical composition as defined in claim 4 or 5, a nutritional supplement as defined in claim 6 or 7 or a feedstuff, a food product, a dietary supplement, or a food additive as defined in claim 8 or 9 for use in reducing disruption to the colon of a subject, preferably said subject has IBD.

According to a seventh aspect of the invention, a *Bacteroides thetaiotaomicron* as defined in claim 1, a composition as defined in claim 2 or 3, a pharmaceutical composition as defined in claim 4 or 5, a nutritional supplement as defined in claim 6 or 7 or a feedstuff, a food product, a dietary supplement, or a food additive as defined in claim 8 or 9 for use in reducing the expression of one or more pro-inflammatory genes in a cell or cells of a subject.

According to an eighth aspect of the invention, a *Bacteroides thetaiotaomicron* as defined in claim 1, a composition as defined in claim 2 or 3, a pharmaceutical composition as defined in claim 4 or 5, a nutritional supplement as defined in claim 6 or 7 or a feedstuff, a food product, a dietary supplement, or a food additive as defined in claim 8 or 9 for use in increasing the percentage of regulatory T cells (Tregs) in the alimentary canal or a section of the alimentary canal.

According to a ninth aspect of the invention, a process for producing a pharmaceutical composition according to claim 4 or 5, said process comprising admixing said *Bacteroides thetaiotaomicron* with a pharmaceutically acceptable excipient, carrier or diluent, wherein said *Bacteroides thetaiotaomicron* is optionally encapsulated in said process.

According to a tenth aspect of the invention, a method for modulating the inflammation of a tissue or an organ in a subject wherein said method comprises administering to the subject a *Bacteroides thetaiotaomicron* as defined in claim 1, a composition as defined in claim 2 or 3, a pharmaceutical composition as defined in claim 4 or 5, a nutritional supplement as defined in claim 6 or 7 or a feedstuff, a food product, a dietary supplement, or a food additive as defined in claim 8 or 9.

According to an eleventh aspect of the invention, a method for treating and/or preventing of an inflammatory disorder and/or an autoimmune disorder in a subject wherein said method comprises administering to the subject a *Bacteroides thetaiotaomicron* as defined in claim 1, a composition as defined in claim 2 or 3, a pharmaceutical composition as defined in claim 4 or 5, a nutritional supplement as defined in claim 6 or 7 or a feedstuff, a food product, a dietary supplement, or a food additive as defined in claim 8 or 9.

According to a twelfth aspect of the invention, a method for reducing disruption to the colon of a subject wherein said method comprises administering to the subject a *Bacteroides thetaiotaomicron* as defined in claim 1, a composition as defined in claim 2 or 3, a pharmaceutical composition as defined in claim 4 or 5, a nutritional supplement as defined in claim 6 or 7 or a feedstuff, a food product, a dietary supplement, or a food additive as defined in claim 8 or 9, preferably wherein the subject has IBD.

According to a thirteenth aspect of the invention, a method for reducing the expression of one or more pro-inflammatory genes in a cell or cells of a subject wherein said method comprises administering to the subject a *Bacteroides thetaiotaomicron* as defined in claim 1, a composition as defined in claim 2 or 3, a pharmaceutical composition as defined in claim 4 or 5, a nutritional supplement as defined in claim 6 or 7 or a feedstuff, a food product, a dietary supplement, or a food additive as defined in claim 8 or 9.

According to a fourteenth aspect of the invention, a method for increasing the percentage of Regulatory T cells (Tregs) in the alimentary canal or a section of the alimentary canal wherein said method comprises administering to the subject a *Bacteroides thetaiotaomicron* as defined in claim 1, a composition as defined in claim 2 or 3, a pharmaceutical composition as defined in claim 4 or 5, a nutritional supplement as defined in claim 6 or 7 or a feedstuff, a food product, a dietary supplement, or a food additive as defined in claim 8 or 9.

According to a fifteenth aspect of the invention, a *Bacteroides thetaiotaomicron* as defined in claim 1, a composition as defined in claim 2 or 3, a pharmaceutical composition as defined in claim 4 or 5, a nutritional supplement as defined in claim 6 or 7 or a feedstuff, a food product, a dietary supplement, or a food additive as defined in claim 8 or 9, for the manufacture of a medicament for modulating the inflammation of a tissue or an organ in a subject.

According to a sixteenth aspect of the invention, a *Bacteroides thetaiotaomicron* as defined in claim 1, a composition as defined in claim 2 or 3, a pharmaceutical composition as defined in claim 4 or 5, a nutritional supplement as defined in claim 6 or 7 or a feedstuff, a food product, a dietary supplement, or a food additive as defined in claim 8 or 9, for the manufacture of a medicament for the treatment and/or prevention of an inflammatory disorder and/or an autoimmune disorder in a subject.

According to a seventeenth aspect of the invention, a *Bacteroides thetaiotaomicron* as defined in claim 1, a composition as defined in claim 2 or 3, a pharmaceutical composition as defined in claim 4 or 5, a nutritional supplement as defined in claim 6 or 7 or a feedstuff, a food product, a dietary supplement, or a food additive as defined in claim 8 or 9 for the manufacture of a medicament for reducing disruption to the colon of a subject, preferably wherein the subject has IBD.

According to an eighteenth aspect of the invention, a *Bacteroides thetaiotaomicron* as defined in claim 1, a composition as defined in claim 2 or 3, a pharmaceutical composition as defined in claim 4 or 5, a nutritional supplement as defined in claim 6 or 7 or a feedstuff, a food product, a dietary supplement, or a food additive as defined in claim 8 or 9 for the manufacture of a medicament for reducing the expression of one or more pro-inflammatory genes in a cell or cells of a subject.

According to a nineteenth aspect of the invention, a *Bacteroides thetaiotaomicron* as defined in claim 1, a composition as defined in claim 2 or 3, a pharmaceutical composition as defined in claim 4 or 5, a nutritional supplement as defined in claim 6 or 7 or a feedstuff, a food product, a dietary supplement, or a food additive as defined in claim 8 or 9 for the manufacture of a medicament for increasing the percentage of Regulatory T cells (Tregs) in the alimentary canal or a section of the alimentary canal.

BRIEF DESCRIPTION OF THE FIGURES

The invention is described with reference to the accompanying figures, wherein.

DETAILED DESCRIPTION OF THE INVENTION

Figure 1:
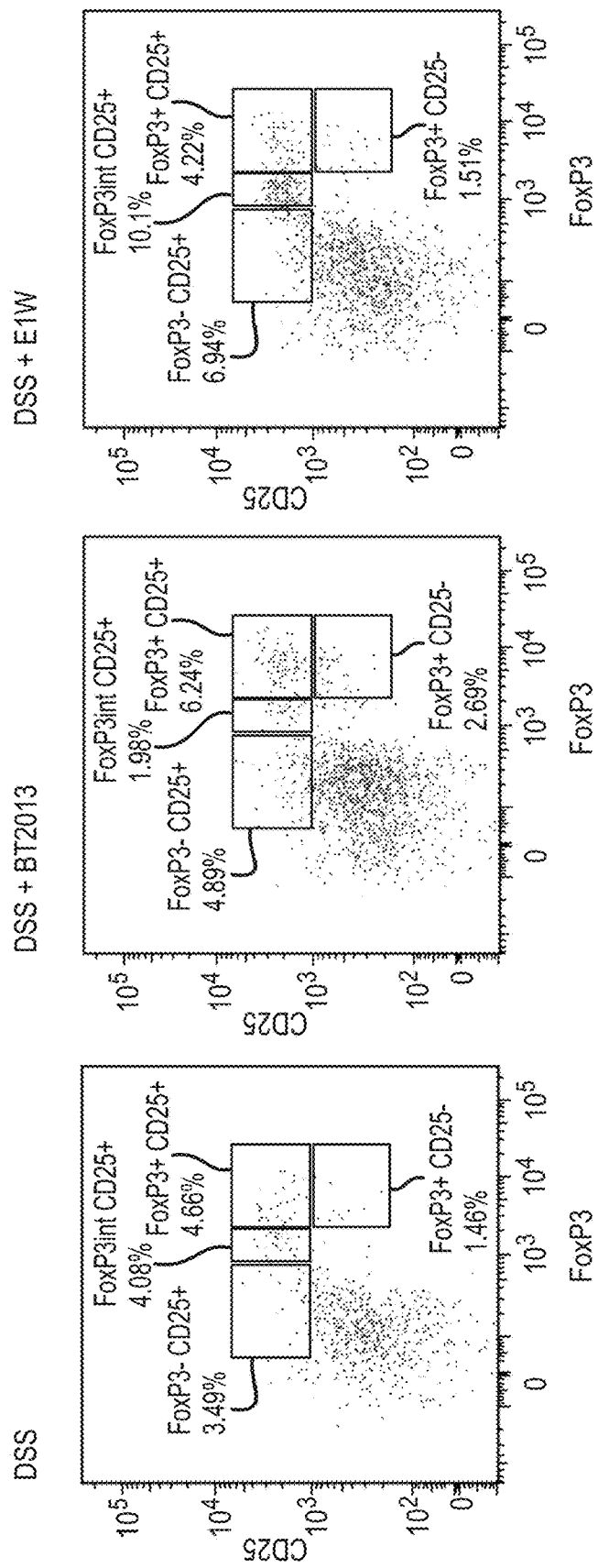
FIG. 1 illustrates the attenuation of colitis via expansion of Treg cells with *B. thetaiotaomicron* strain BT2013 in a DSS induced colitis model.
Figure 1:
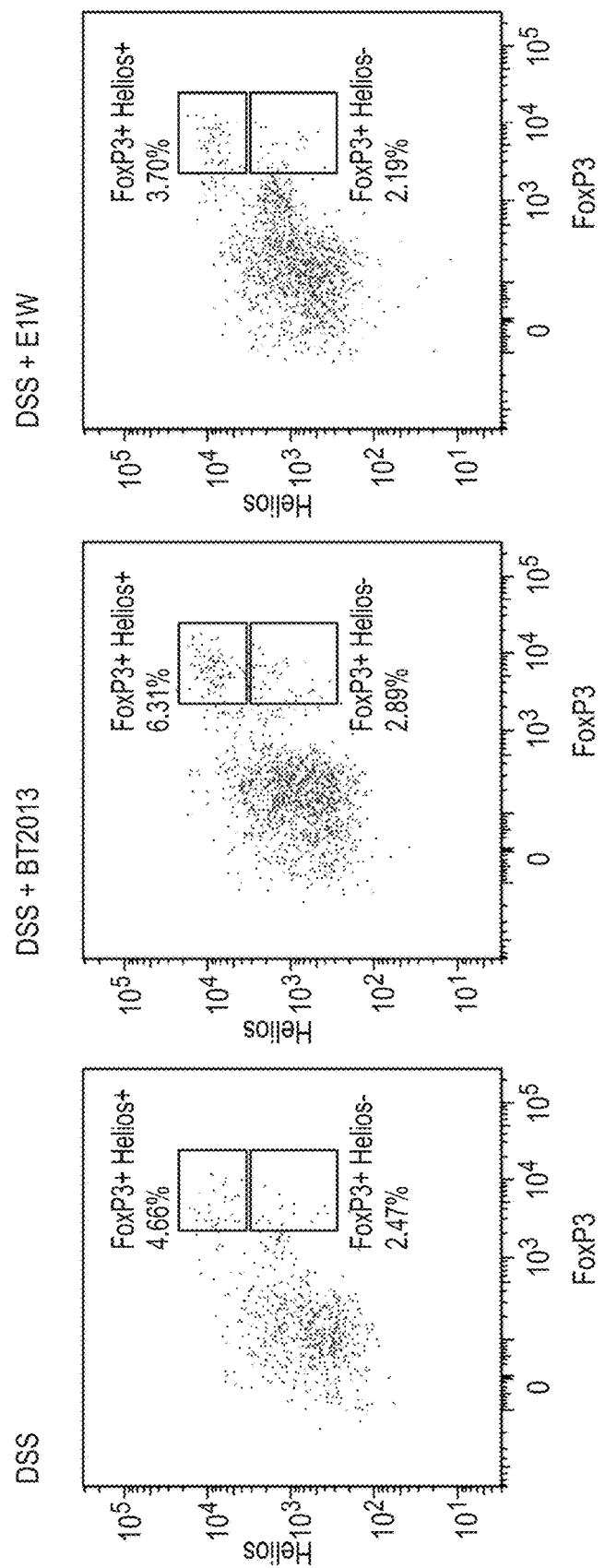
Figure 1:
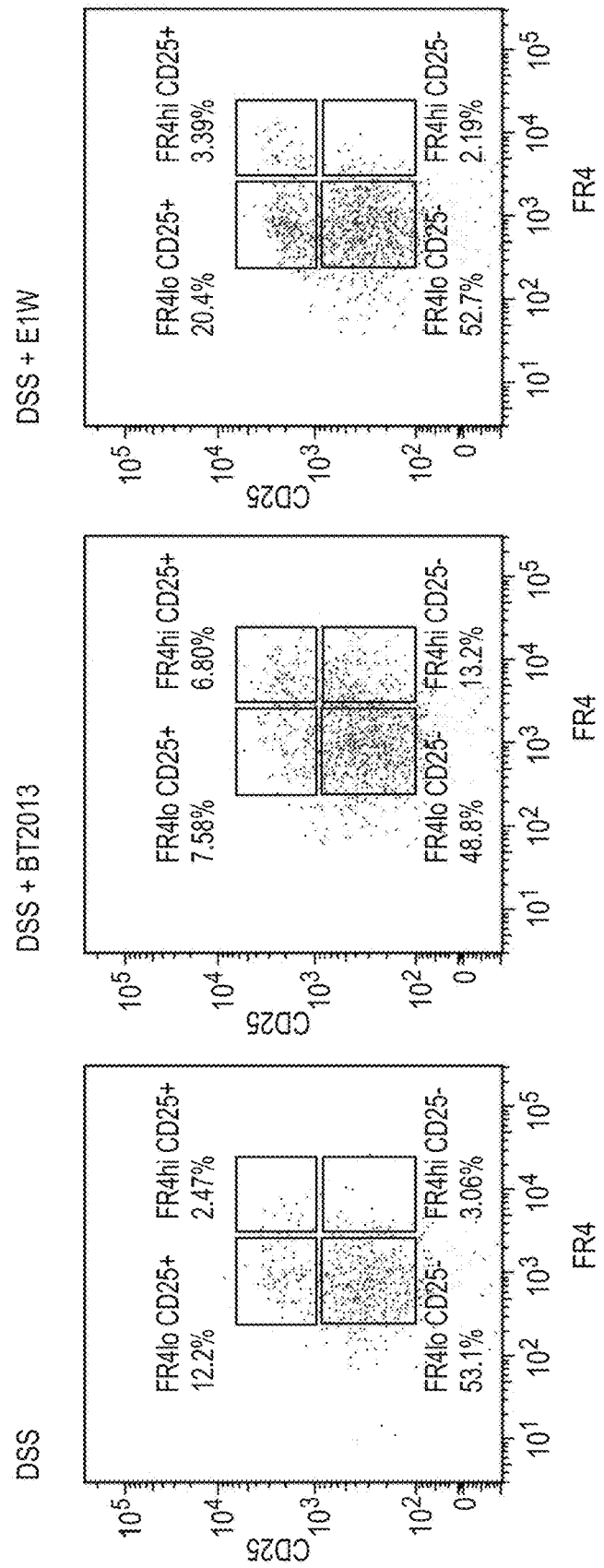

The present invention is based on the finding that BT strain BT2013 has more potent anti-inflammatory effects compared to control BT strains.

BT strain BT2013 has been deposited under Accession number 42341 on 3 Dec. 2014 at National Collections of Industrial, Food and Marine Bacteria (NCIMB) at NCIMB Ltd, Ferguson Building, Craibstone Estate, Bucksburn, Aberdeen, UK, AB21 9YA. The deposit was made under the terms of the Budapest Treaty. Maintenance of a viable culture is assured for 30 years from the date of the deposits. All restrictions on the availability to the public of the deposited microorganism will be irrevocably removed upon the granting of a patent for this application. The deposit was made by GT Biologics Ltd. (Life Sciences Innovation Building, Aberdeen, AB25 2ZS, Scotland). GT Biologics Ltd. has subsequently changed its name to 4D Pharma Research Limited.

Derivative

The present invention encompasses derivatives of the deposited strain. The term "derivative" includes daughter strains (progeny) or stains cultured (sub-cloned) from the original but modified in some way (including at the genetic level), without altering negatively the biological activity, i.e. the derivative strain will have at least the same immune modulatory activity as the original BT2013 strain.

Biotypes

A genome sequence for strain BT2013 is provided in SEQ ID NO:1.

Bacterial strains that are biotypes of the bacterium deposited under accession number NCIMB 42341 are also expected to be effective for treating or preventing inflammatory disorders and/or autoimmune disorders and/or allergic disorders. A biotype is a closely related strain that has the same or very similar physiological and biochemical characteristics.

In certain embodiments, the bacterial strain for use in the invention has a 16s rRNA sequence that is at least 95%, 96%, 97%, 98%, 99%, 99.5% or 99.9% identical to the 16s rRNA sequence of the bacterium deposited under accession number NCIMB 42341.

Alternatively, strains that are biotypes of the bacterium deposited under accession number NCIMB 42341 and that are suitable for use in the invention may be identified by sequencing other nucleotide sequences for the bacterium deposited under accession number NCIMB 42341. For example substantially the whole genome may be sequenced and a biotype strain for use in the invention may have at least 95%, 96%, 97%, 98%, 99%, 99.5% or 99.9% sequence identity across at least 80% of its whole genome (e.g. across at least 85%, 90%, 95% or 99%, or across its whole genome). Other suitable sequences for use in identifying biotype strains may include hsp60 or repetitive sequences such as BOX, ERIC, (GTG)$_5$, or REP (Masco et al. (2003) Systematic and Applied Microbiology, 26:557-563). Biotype strains may have sequences with at least 95%, 96%, 97%, 98%, 99%, 99.5% or 99.9% A sequence identity to the corresponding sequence of the bacterium deposited under accession number NCIMB 42341.

In certain embodiments, the bacterial strain for use in the invention has a genome with sequence identity to SEQ ID NO:1. In preferred embodiments, the bacterial strain for use in the invention has a genome with at least 90% sequence identity (e.g. at least 92%, 94%, 95%, 96%, 97%, 98%, 99% A or 100% sequence identity) to SEQ ID NO:1 across at least 60% (e.g. at least 65%, 70%, 75%, 80%, 85%, 95%, 96%, 97%, 98%, 99% A or 100%) of SEQ ID NO:1. For example, the bacterial strain for use in the invention may have a genome with at least 90% sequence identity to SEQ ID NO:1 across 70% of SEQ ID NO:1, or at least 90% sequence identity to SEQ ID NO:1 across 80% of SEQ ID NO:1, or at least 90% sequence identity to SEQ ID NO:1 across 90% of SEQ ID NO:1, or at least 90% sequence identity to SEQ ID NO:1 across 100% of SEQ ID NO:1, or at least 95% sequence identity to SEQ ID NO:1 across 70% of SEQ ID NO:1, or at least 95% sequence identity to SEQ ID NO:1 across 80% of SEQ ID NO:1, or at least 95% sequence identity to SEQ ID NO:1 across 90% of SEQ ID NO:1, or at least 95% sequence identity to SEQ ID NO:1 across 100% of SEQ ID NO:1, or at least 98% sequence identity to SEQ ID NO:1 across 70% of SEQ ID NO:1, or at least 98% sequence identity to SEQ ID NO:1 across 80% of SEQ ID NO:1, or at least 98% sequence identity to SEQ ID NO:1 across 90% of SEQ ID NO:1, or at least 98% sequence identity to SEQ ID NO:1 across 100% of SEQ ID NO:1.

Alternatively, strains that are biotypes of the bacterium deposited under accession number NCIMB 42341 and that are suitable for use in the invention may be identified by using the accession number NCIMB 42341 deposit and restriction fragment analysis and/or PCR analysis, for example by using fluorescent amplified fragment length polymorphism (FAFLP) and repetitive DNA element (rep)-PCR fingerprinting, or protein profiling, or partial 16S or 23s rDNA sequencing.

In certain embodiments, strains that are biotypes of the bacterium deposited under accession number NCIMB 42341 and that are suitable for use in the invention are strains that provide the same pattern as the bacterium deposited under accession number NCIMB 42341 when analysed by amplified ribosomal DNA restriction analysis (ARDRA), for example when using Sau3AI restriction enzyme (for exemplary methods and guidance see, for example, Srůtková et al. (2011) J. Microbiol. Methods, 87(1):10-6). Alternatively, biotype strains are identified as strains that have the same carbohydrate fermentation patterns as the bacterium deposited under accession number NCIMB 42341.

Bacterial strains that are biotypes of the bacterium deposited under accession number NCIMB 42341 and that are useful in the compositions and methods of the invention may be identified using any appropriate method or strategy. For example, bacterial strains that have similar growth patterns, metabolic type and/or surface antigens to the bacterium deposited under accession number NCIMB 42341 may be useful in the invention. A biotype strain will have comparable immune modulatory activity to the NCIMB 42341 strain. For example, a biotype strain will elicit comparable effects on the DSS-induced colitis models and comparable effects on Treg levels, MPO enzymatic activity, inflammation-associated gene expression and colon histopathology to the effects shown in the Functional Assays, which may be identified by using the protocols described in the Functional Assays.

Disorders

The *Bacteroides thetaiotaomicron* strain BT2013 may be used for the treatment and/or prevention of a disorder in a subject, wherein said disorder is an inflammatory disorder and/or an autoimmune disorder.

In one embodiment, the disorder affects the alimentary canal, a section of the alimentary canal, the liver, liver cells, immune cells, epithelial cells, epidermal cells, neuronal cells, endothelial cells, fibroblasts, the pancreas, and/or pancreatic cells (such as the islets of Langerhans).

Examples of sections (i.e. parts) of the alimentary canal include the oesophagus, the stomach and the intestine (such as the small intestine (e.g. the duodenum, the jejunum and the ileum) and/or the large intestine (e.g. the caecum, ascending colon, transverse colon, descending colon, and sigmoid colon)).

Examples of epithelial cells include intestinal epithelial cells. Examples of immune cells include dendritic cells, monocytes/macrophages, Tcells and neutrophils.

In one embodiment, the disorder is selected from the group consisting of:

1. Organ associated disorders such as irritable bowel syndrome (IBS), inflammatory bowel disease including Crohn's disease and ulcerative colitis, necrotising enterocolitis, pouchitis, coeliac disease, multiple sclerosis (brain), type I diabetes, Goodpasture's syndrome, Hashimoto thyroiditis, chronic active hepatitis, cardiomyopathy, uveitis and rhinitis.

2. Systemic disorders such as rheumatoid arthritis, systemic lupus erythematosus, scleroderma, psoriasis, atopic dermatitis, vitiligo, multiple sclerosis, alopecia areata, sarcoidosis, polymyositis and combinations thereof.

In one aspect, the disorder affects the intestine.

In one aspect, the disorder is an inflammatory disorder. For example, the disorder is an inflammatory bowel disorder (IBD) such as Crohn's disease.

In one aspect, the disorder is an autoimmune disorder. For example, the autoimmune disorder is selected from the group consisting of ulcerative colitis, pouchitis, rheumatoid arthritis, psoriasis, multiple sclerosis, type I diabetes, allergies (including coeliac disease), atopic dermatitis and rhinitis.

Subject

In one embodiment, the subject is a monogastric animal.

Examples of monogastric animals include poultry, humans, rats, pigs, dogs, cats, horses and rabbits.

In another embodiment, the subject is a mammal such as a monogastric mammal.

Examples of monogastric mammals include omnivores (such as humans, rats, and pigs), carnivores (such as dogs and cats), and herbivores (such as horses and rabbits).

Preferably, the subject is a human.

In one aspect, the subject has a disorder is selected from the group consisting of inflammatory bowel disorder (IBD), colitis, rheumatoid arthritis, psoriasis, multiple sclerosis, type I diabetes, coeliac disease, atopic dermatitis, rhinitis, irritable bowel syndrome (IBS), ulcerative colitis, pouchitis, Crohn's disease, functional dyspepsia, atopic diseases, necrotising enterocolitis, non alcoholic fatty liver disease, gastrointestinal infection and combinations thereof. For example, the subject has IBD.

Modulation/Regulation

The terms "modulation" and "regulation" may be used interchangeably herein.

In one embodiment The *B. thetaiotaomicron* strain BT2013 is used to modulate the inflammation of a cell, a tissue or an organ in a subject.

In one embodiment, the term "modulation" refers to an increase and/or induction and/or promotion and/or activation. In an alternative embodiment, the term "modulation" refers to a decrease and/or reduction and/or inhibition.

In one embodiment, the term "regulation" refers to an upregulation. In an alternative embodiment, the term "regulation" refers to a downregulation.

In one embodiment, the *B. thetaiotaomicron* strain BT2013 as described herein reduces the inflammation of a cell, a tissue or an organ. For example, inflammation of the alimentary canal, a section (i.e. part) of the alimentary canal (such as the intestine), the liver, liver cells, epithelial cells, epidermal cells, neuronal cells, endothelial cells, fibroblasts, the pancreas, and/or pancreatic cells (such as the islets of Langerhans) is reduced.

In one example, inflammation of the alimentary canal or part thereof (such as the intestine) is reduced.

In another example, inflammation by immune cells of the tissue or the organ is reduced.

In another example, inflammation by epithelial cells of the tissue or the organ is reduced.

The term "inflammation" as used herein refers to one or more of the following: redness, swelling, pain, tenderness, heat, and disturbed function of a cell, a tissue or organ due to an inflammatory process triggered by over-reaction of the immune system.

In one embodiment, the numbers of cells which are inflamed in a subject is at least 10%, 20%, 30%, 40% or 50% lower after administration of the polypeptide or polynucleotide or host cell as described herein when compared to the numbers of cells which are inflamed in a subject before the strain BT2013 as described herein is administered to the subject.

In one embodiment, the amount of a tissue or organ which is inflamed in a subject is at least 10%, 20%, 30%, 40% or 50% lower after administration of strain BT2013 when compared to the amount of tissue or organ which is inflamed in a subject before the strain BT2013 is administered to the subject.

In one embodiment, the strain BT2013 reduces the inflammation by epithelial cells of the tissue or the organ.

For example, the epithelial cells are epithelial cells of the alimentary canal or part thereof (such as the intestine).

Without wishing to be bound by theory, the strain BT2013 increases the production of T cells (such as regulatory T cells which may also be referred to as Tregs) in a subject. This increase in Treg numbers may combat the effects of other effector T cells (also referred to as Teffs), such as Th1, Th17 and Th2 which drive inflammation, autoimmunity and allergic/atopic conditions. In Crohn's disease and ulcerative colitis the Teff/Treg cell balance is lost.

In one embodiment, the production of T cells in a subject is increased such that there are at least 10%, 20%, 30%, 40% or 50% more T cells, or greater than 100% more T cells after administration of the polypeptide or polynucleotide or host cell as described herein when compared to the number of T cells in the subject before the strain BT2013 is administered to the subject.

Intestine Barrier Integrity

In one embodiment, the strain BT2013 is used to improve intestine barrier integrity in a subject.

The term "improving intestine barrier integrity" as used herein refers to a reduction in the numbers and/or types of microorganisms which spread from the intestine into other cells in a subject after administration of the strain BT2013 when compared to the numbers and/or types of microorganisms which spread from the intestine into other cells in a subject before administration of the strain BT2013 as described herein.

In one embodiment, the numbers of microorganisms which spread from the intestine into other cells in a subject are at least 10%, 20%, 30%, 40% or 50% lower after administration of the strain BT2013 when compared to the numbers of microorganisms which spread from the intestine into other cells in a subject administration.

In one embodiment, there are at least 5%, 10%, 15% or 20% fewer types of microorganisms which spread from the intestine into other cells in a subject after administration of the strain BT2013 when compared to the types of microorganisms which spread from the intestine into other cells in a subject before the administration.

Intestine Disruption

In one embodiment strain BT2013, is used to reduce disruption to the intestine (e.g. large intestine) of a subject (such as a subject with IBD).

The term "disruption to the intestine of a subject" as used herein refers to an affect on the integrity of the mucosal epithelium and/or an affect on the number of goblet cells in the epithelium and/or an affect on the number of immune cells infiltrating the lamina propria.

In one embodiment, strain BT2013 reduces or prevents disruption to the integrity of the mucosal epithelium and/or reduces or prevents a reduction in the number of goblet cells in the epithelium and/or reduces or prevents the infiltration of immune cells into the lamina propria.

In one embodiment, a reduction in disruption to the integrity of the mucosal epithelium is a reduction of at least 5%, 10%, 15% or 20% in the numbers of bacteria crossing from the intestinal lumen into intestinal cells after administration of strain BT2013 when compared to the numbers of bacteria crossing from the intestinal lumen into intestinal cells in a subject before administration.

In one embodiment, a reduction in the number of goblet cells in the epithelium is a reduction of at least 2%, 5%, 10%, 15% or 20% in the numbers of goblet cells in the epithelium of a subject after administration of strain BT2013 when compared to the number of goblet cells in the epithelium of a subject before administration.

In one embodiment, the reduction in the infiltration of immune cells into the lamina propria is such that over a fixed time period (such as 24 hours) there is a reduction of at least 5%, 10%, 15%, 20% or 30% in the numbers of immune cells (e.g. T cells) crossing into lamina propria cells after administration of strain BT2013 when compared to the numbers of immune cells (e.g. T cells) crossing into the lamina propria in a subject before administration.

Pro-Inflammatory Genes and Barrier Integrity Genes

In one embodiment, strain BT2013 is used to regulate the expression of one or more pro-inflammatory genes and/or one or more barrier integrity genes in a cell or cells of a subject.

In one embodiment, the term "regulate" refers to an upregulation in the expression of one or more pro-inflammatory genes. In an alternative embodiment, the term "regulate" refers to a downregulation in the expression of one or more pro-inflammatory genes.

In one embodiment, strain BT2013 downregulates the expression of one or more pro-inflammatory genes in a cell or cells of a subject.

The term "pro-inflammatory gene" as used herein refers to a gene which, when expressed, promotes inflammation. Examples of pro-inflammatory genes include genes encoding but not limited to IL1-β, IL4, IL5, IL6, IL8, IL12, IL13, IL17, IL21, IL22, IL23, IL27, IFN, CCL2, CCL3, CCL5, CCL20, CXCL5, CXCL10, CXCL12, CXCL13, and TNF-α.

In one embodiment, the pro-inflammatory gene is selected from the group consisting of IL1-β, IL6 and IL8.

In one embodiment, the expression level (e.g. mRNA level) of one or more pro-inflammatory genes is decreased (i.e. downregulated) such that the level is at least 10%, 20%, 30%, 40% or 50% lower after administration of the strain BT2013 when compared to the level in the subject before administration.

The term "barrier integrity genes" as used herein refers to a gene which, when expressed, has a role in the function of the barrier of the intestine such as the repair of the barrier and the prevention of microorganisms crossing the barrier. Examples of barrier integrity genes include genes encoding Retnlg|Retnlb, Si, Defa24, Hsd11b2, Hsd17b2, and Nr1d1|Thra.

In one embodiment, the term "regulate" refers to an upregulation in the expression of one or more barrier integrity genes. In an alternative embodiment, the term "regulate" refers to a downregulation in the expression of one or more barrier integrity genes.

In one embodiment, strain BT2013 upregulates the expression of barrier integrity genes in a cell or cells of a subject In one embodiment, the barrier integrity gene is selected from the group consisting of Retnlg|Retnlb, Si, Defa24, Hsd11b2, Hsd17b2, and Nr1d1|Thra.

In one embodiment, the expression level (e.g. mRNA level) of one or more barrier integrity genes is increased (i.e. upregulated) such that the level is at least 10%, 20%, 30%, 40% or 50% higher after administration of strain BT2013 when compared to the level in the subject before administration.

Alimentary Canal

Parts of the alimentary canal include the oesophagus, the stomach and the intestine (such as the small intestine (e.g. the duodenum, the jejunum and the ileum) and/or the large intestine (e.g. the caecum, ascending colon, transverse colon, descending colon, and sigmoid colon)).

Herein, the term "large intestine" may be used interchangeably with the term "colon".

In one embodiment, strain BT2013 is used for improving alimentary canal health in a subject.

The term "improving alimentary canal health" as used herein refers to reducing the level of inflammation in the alimentary canal or part thereof and/or improving intestinal microbiota.

In one embodiment, the level of inflammation in the alimentary canal is at least 10%, 20%, 30%, 40% or 50% lower after administration of strain BT2013 when compared to the level of inflammation in the alimentary canal of a subject before administration.

In one embodiment, strain BT2013 is used for improving intestinal microbiota in a subject.

The term "intestinal microbiota" as used herein refers to microorganisms that live in the digestive tract of the host animals. These microorganisms perform a wide variety of metabolic, structural, protective and other beneficiary functions.

As used herein, the term "improving intestinal microbiota" refers to increasing the number and/or type of desirable microorganisms present in the intestine of a subject (e.g. the host), and/or increasing the activity of said desirable microorganisms in terms of their metabolic, structural, protective and other beneficiary functions. The term "improving intestinal microbiota" may also refer to decreasing the number and/or type of undesirable microorganisms present in the intestine of a subject (e.g. the host), and/or decreasing the activity of said undesirable microorganisms in terms of their metabolic, structural, protective and other beneficiary functions.

Microorganisms which are desirable in the intestine of a host are those microorganisms which have a protective and beneficiary function. Firmicutes and bacteroidetes bacteria are examples of desirable microorganisms in the intestine of a host.

Microorganisms which are undesirable in the intestine of a host are those microorganisms which can interfere with the metabolic, structural, protective and other beneficiary functions of desirable microorganisms in the intestine have a protective and beneficiary function. In addition or alternatively, undesirable microorganisms are those which cause, for example, inflammation and/or diarrhea. *E. coli* is an example of an undesirable microorganism in the intestine of a host.

For example, a change in the microbiota balance between desirable microorganism (such as firmicutes and bacteroidetes bacteria) and undesirable microorganisms (such as *E. coli*: ETEC, EPEC, EIEC, EHEC and EAEC) within the intestine may occur in subjects with inflammatory bowel disease (IBD) once strain BT2013 has been administered to the subject.

In one embodiment, the number of desirable microorganisms (such as firmicutes and bacteroidetes bacteria) present in the intestine of a subject (e.g. the host), is increased such that the number of microorganisms is at least 10%, 20%, 30%, 40% or 50% higher, or greater than 100% higher after administration of the strain BT2013 compared to the level in the subject before administration. In addition, or alternatively, the types of desirable microorganisms (such as firmicutes and bacteroidetes) present in the intestine of a subject (e.g. the host), are increased such that there are at least 2%, 5%, 10%, or 15% more types of microorganisms after administration of strain BT2013 when compared to the types in the subject before administration.

In one embodiment, the number of undesirable microorganisms (such as *E. coli* ETEC, EPEC, EIEC, EHEC and EAEC) present in the intestine of a subject (e.g. the host), is decreased such that the number of microorganisms is at least 10%, 20%, 30%, 40% or 50% lower after administration strain BT2013 when compared to the level in the subject before administration. In addition, or alternatively, the types of undesirable microorganisms (such as *E. coli* ETEC, EPEC, EIEC, EHEC and EAEC) present in the intestine of a subject (e.g. the host), are decreased such that there are at least 1%, 2%, 5%, or 10%, fewer types of undesirable microorganisms after administration of strain BT2013 when compared to the types in the subject before administration.

Encapsulation

In one embodiment, the *B. thetaiotaomicron* strain BT2013 is encapsulated.

In a further embodiment, a pharmaceutical composition comprising the strain BT2013 is encapsulated.

In another embodiment, a nutritional supplement comprising the strain BT2013 is encapsulated.

In a further embodiment, a feedstuff, food product, dietary supplement, or food additive as described herein is encapsulated.

The term "encapsulated" as used herein refers to a means for protecting the strain BT2013 from an incompatible environment by physical separation so that it can be delivered to the target site (e.g. the intestine) without degradation or significant degradation in order that the strain BT2013 can have an effect on the target site. An example is an enteric coated capsule or an enterically-resistant capsule.

Even when the objective of the encapsulation is the isolation of the strain from its surroundings, the protective coating or shell must be ruptured at the time of desired action. The rupturing of the protective coating or shell is typically brought about through the application of chemical and physical stimuli such as pressure, enzyme attack, chemical reaction and physical disintegration.

For example, encapsulation ensures that the strain can be ingested so that the microorganisms can be delivered to the target site (e.g. the intestine) in an amount which is effective to produce an effect at the target site.

Pharmaceutical Composition

In one embodiment, a pharmaceutical composition comprises microorganisms of the strain BT2013 and optionally a pharmaceutically acceptable excipient, carrier or diluent.

The pharmaceutical composition may be any pharmaceutical composition. In one aspect, the pharmaceutical composition is to be administered orally, enterally or rectally. For example, the composition may be an edible composition. "Edible" means a material that is approved for human or animal consumption.

The pharmaceutical compositions may be for human or animal usage in human and veterinary medicine.

Examples of such suitable excipients for the various different forms of pharmaceutical compositions described herein may be found in the "Handbook of Pharmaceutical Excipients, 2nd Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like.

Examples of suitable diluents include one or more of: water, ethanol, glycerol, propylene glycol and glycerin, and combinations thereof.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavouring agents may be provided in the pharmaceutical composition. Examples of preservatives include sodium benzoate, sorbic acid and esters of p-hydroxybenzoic acid. Antioxidants and suspending agents may be also used.

In one aspect, the microorganisms of strain BT2013 pharmaceutical composition are encapsulated.

The pharmaceutical may be in the form of a solution or as a solid—depending on the use and/or the mode of application and/or the mode of administration.

As used herein, the term "medicament" encompasses medicaments for both human and animal usage in human and veterinary medicine. In addition, the term "medicament" as used herein means any substance, which provides a therapeutic and/or beneficial effect. The term "medicament" as used herein is not necessarily limited to substances, which need Marketing Approval, but may include substances which, can be used in cosmetics, nutraceuticals, food (including feeds and beverages for example), probiotic cultures, nutritional supplements and natural remedies. In addition, the term "medicament" as used herein encompasses a product designed for incorporation in animal feed, for example livestock feed and/or pet food.

Nutritional Supplements

Nutritionally acceptable carriers, diluents and excipients include those suitable for human or animal consumption and that are used as standard in the food industry. Typical nutritionally acceptable carriers, diluents and excipients will be familiar to the skilled person in the art.

In one embodiment, a nutritional supplement comprises microorganisms of strain BT2013 or a host cell comprising an expression vector comprising said polynucleotide sequence, and a nutritional acceptable excipient, carrier or diluent.

In one example, the microorganisms of strain BT2013 are encapsulated.

Feedstuff/Products

A further aspect of the invention relates to feedstuffs, food products, dietary supplements and food additives comprising microorganisms of strain BT2013.

The terms "feedstuff", "food product" "food additive" and "dietary supplement" as used herein are intended to cover all consumable products that can be solid, jellied or liquid.

The term "food product" is used in a broad sense—and covers food for humans as well as food for animals (i.e. a feed). In one aspect, the food product is for human consumption. Examples of food products include diary products (such as milk, cheese, beverages comprising whey protein, milk drinks, lactic acid bacteria drinks, yoghurt, drinking yoghurt), bakery products, beverages and beverage powders.

The "feedstuff", "food product" "food additive" and "dietary supplement" may be in the form of a solution or as a solid—depending on the use and/or the mode of application and/or the mode of administration.

As used herein the term "dietary supplement" includes a formulation which is or can be added to a food product or feedstuff as a nutritional supplement. The term "dietary supplement" as used here also refers to formulations which can be used at low levels in a wide variety of products that require gelling, texturising, stabilising, suspending, film-forming and structuring, retention of juiciness and improved mouthfeel, without adding viscosity.

Suitable food products may include, for example, functional food products, food compositions, pet food, livestock feed, health foods, feedstuffs and the like. In one aspect, the food product is a health food.

As used herein, the term "functional food product" means food that is capable of providing not only a nutritional effect, but is also capable of delivering a further beneficial effect to the consumer. Accordingly, functional foods are ordinary foods that have components or ingredients (such as those described herein) incorporated into them that impart to the food a specific functional—e.g. medical or physiological benefit—other than a purely nutritional effect.

Examples of specific food products that are applicable to the present invention include milk-based products, ready to eat desserts, powders for re-constitution with, e.g., milk or water, chocolate milk drinks, malt drinks, ready-to-eat dishes, instant dishes or drinks for humans or food compositions representing a complete or a partial diet intended for pets or livestock.

In one aspect, the feedstuff, food product, dietary supplement or food additive according to the present invention are intended for humans, pets or livestock such as monogastric animals. The feedstuff, food product, dietary supplement or food additive may be intended for animals selected from the group consisting of dogs, cats, pigs, horses, or poultry. In a further embodiment, the food product, dietary supplement or food additive is intended for adult species, in particular human adults.

The term "milk-based product" as used herein means any liquid or semi-solid milk or whey based product having a varying fat content. The milk-based product can be, e.g., cow's milk, goat's milk, sheep's milk, skimmed milk, whole milk, milk recombined from powdered milk and whey without any processing, or a processed product, such as yoghurt, curdled milk, curd, sour milk, sour whole milk, butter milk and other sour milk products. Another important group includes milk beverages, such as whey beverages, fermented milks, condensed milks, infant or baby milks; flavoured milks, ice cream; milk-containing food such as sweets.

The feedstuffs, food products, dietary supplements or food additives of the present invention may be—or may be added to—food supplements, also referred to herein as dietary or nutritional supplements or food additives.

The feedstuffs, food products, dietary supplements or food additives according to the invention may also be used in animal nutrition (e.g. in pig nutrition), particularly in the early-weaned period and growing fattening period. The feedstuffs, food products, dietary supplements or food additives are expected to enhance immune function reduce and prevent infectious diseases, beneficially alter the microbiota composition, and improve growth and performance of animals, for example, through increased feed conversion efficiency.

In one embodiment the feedstuff, food product, dietary supplement, or food additive is encapsulated.

Live Biotherapeutic Product

The microorganisms of strain BT2013 may be used in or as a live biotherapeutic product (LBP).

In one aspect, the LBP is an orally administrable composition of metabolically active, i.e., live and/or lyophilized, or non-viable heat-killed, irradiated or lysed bacteria. The LBP may contain other ingredients. The LBP can be administered orally, i.e., in the form of a tablet, capsule or powder. The LBP may additionally comprise other bacterial species, for example, the bacterial species $R.$ $hominis$. Encapsulated products are favoured for $R.$ $hominis$ as it is an anaerobe. Other ingredients (such as vitamin C, for example), may be included as oxygen scavengers and substrates (such as these improve the colonisation and survival in vivo). Alternatively, the LBP of the invention may be administered orally as a food or nutritional product, such as milk or whey based fermented dairy product, or as a pharmaceutical product.

A suitable daily dose of the bacteria in the LBP is from about $1 \times 10^3$ to about $1 \times 10^{12}$ colony forming units (CFU); for example, from about $1 \times 10^7$ to about $1 \times 10^{10}$ CFU; in another example from about $1 \times 10^6$ to about $1 \times 10^{10}$ CFU.

In one aspect, the LBP contains the bacterial species and/or cellular components thereof, as active ingredients, in an amount of from about $1 \times 10^6$ to about $1 \times 10^{12}$ CFU/g, respect to the weight of the composition; for example, from about $1 \times 10^8$ to about $1 \times 10^{10}$ CFU/g. Typically, a LBP is optionally combined with at least one suitable prebiotic compound. A prebiotic is usually a non-digestible carbohydrate such as an oligo- or polysaccharide, or a sugar alcohol, which is not degraded or absorbed in the upper digestive tract. Known prebiotics include commercial products such as inulin and transgalacto-oligosaccharides.

In one aspect, the LBP of the present description includes a prebiotic in an amount of from about 1 to about 30% by weight, respect to the total weight composition, (e.g. from 5 to 20% by weight). Carbohydrates may be selected from the group consisting of: fructo-oligosaccharides (or FOS), short-chain fructo-oligosaccharides, inulin, isomalt-oligosaccharides, pectins, xylo-oligosaccharides (or XOS), chitosan-oligosaccharides (or COS), beta-glucans, arable gum modified and resistant starches, polydextrose, D-tagatose, acacia fibers, carob, oats, and citrus fibers. In one aspect, the prebiotics are the short-chain fructo-oligosaccharides (for simplicity shown hereinbelow as FOSs-c.c); said FOSs-c.c. are not digestible carbohydrates, generally obtained by the conversion of the beet sugar and including a saccharose molecule to which three glucose molecules are bonded.

Administration

The pharmaceutical compositions, the nutritional supplements, feedstuffs, food products, dietary supplements or food additives of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

In one aspect, the pharmaceutical compositions, the nutritional supplements, feedstuffs, food products, dietary supplements or food additives of the present invention are adapted for oral, rectal, vaginal, parenteral, nasal, buccal or sublingual routes of administration.

In a further aspect, the pharmaceutical compositions, the nutritional supplements, feedstuffs, food products, dietary supplements or food additives of the present invention are adapted for oral administration.

For oral administration, particular use is made of compressed tablets, pills, tablets, gellules, drops, and capsules.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries and suspensions. Pharmaceutical compositions, the nutritional supplements, feedstuffs, food products, dietary supplements or food additives may be formulated in unit dosage form, i.e., in the form of discrete portions containing a unit dose, or a multiple or sub-unit of a unit dose.

Dosage

A person of ordinary skill in the art can easily determine an appropriate dosage amount of the strain BT2013 to administer to a subject without undue experimentation. Typically, a physician will determine the actual dosage which will be most suitable for an individual patient and it will depend on a variety of factors including the activity of the strain employed, the metabolic stability and length of action of that strain, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Combinations

In one aspect, microorganisms of strain BT2013 are administered in combination with one or more other active agents. In such cases, the microorganisms of strain BT2013 may be administered consecutively, simultaneously or sequentially with the one or more other active agents.

Functional Assays:

In Vivo Model

C57BL/6 mice (6 weeks old) were used to evaluate the therapeutic effect of *B. thetaiotaomicron* strains E1, E2 and BT2013 during DSS-induced colitis. The mice were colonised with one of the *B. thetaiotaomicron* strains prior to treatment with DSS. The animals were euthanized and intestinal tissue sampling was performed. Small intestine was collected for immunological analysis by flow cytometry and enzymatic activity measurements of the enzyme myeloperoxidase (MPO). Ascending colon were divided into equal parts and transferred to neutral buffered formalin (NBF; Sigma-Aldrich) for histological analysis or RNAlater (Ambion) for molecular analysis.

Figure 2:
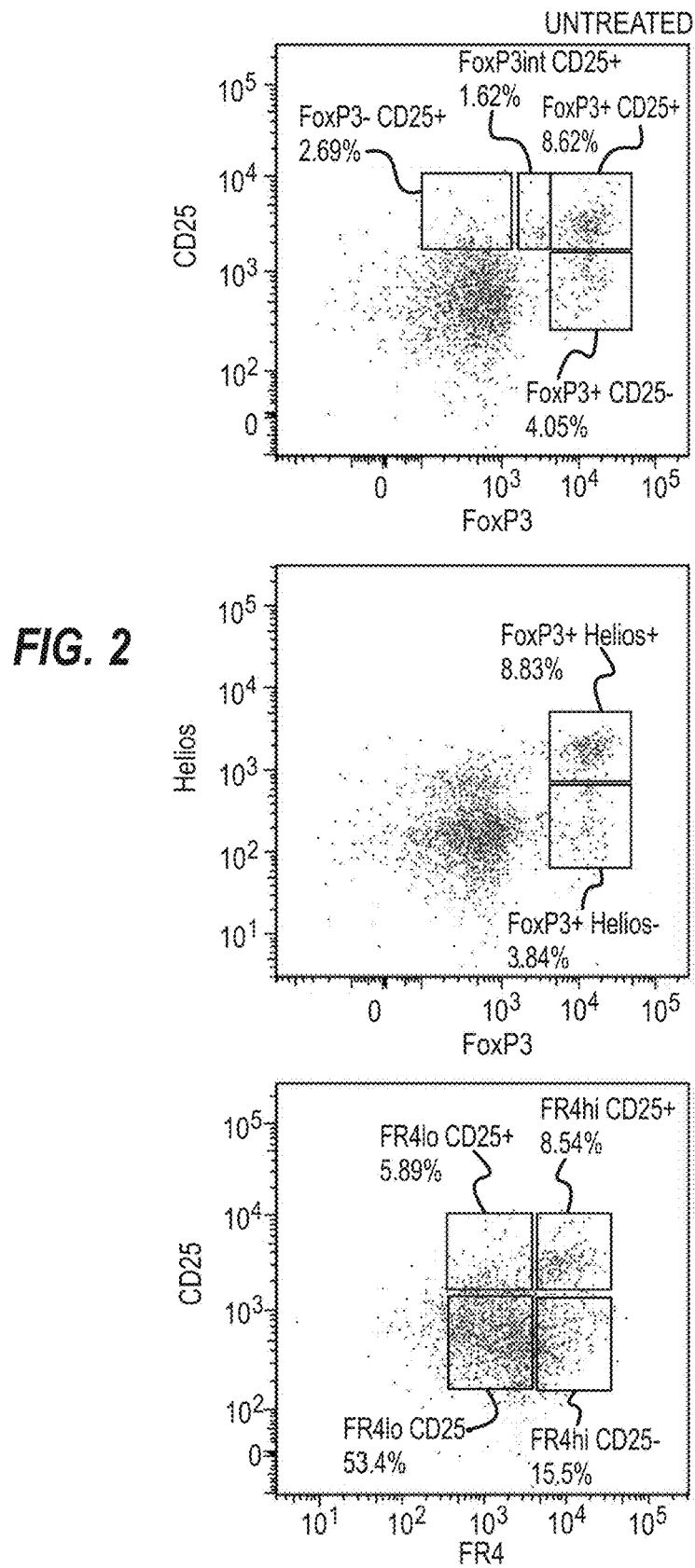
FIG. 2 illustrates that *B. thetaiotaomicron* strain BT2013 does not influence Treg cells, but influences Teff cells, in conventional mice.

Flow cytometry analysis of T cell populations in small intestine lamina propria was carried out (FIG. 1 and FIG. 2). DSS alone and *B. thetaiotaomicron* treatment did not affect the total percentage of the CD3+CD4+CD8-population. The populations influenced by DSS alone and *B. thetaiotaomicron* were the Tregs (CD25+FoxP3+* and FR4$^{hi}$CD25+*) and Teff cells (FR4$^{lo}$ CD25+*) (FIGS. 1 and 2). The percentage of Tregs was increased in mice treated with *B. thetaiotaomicron* strain BT2013 compared to DSS alone. The strain E1W did not appear to have any effect on Tregs. (FIG. 1). The effects of BT2013 in Tregs were only apparent in mice co-treatment with DSS. The strain had no effect on Tregs in untreated mice but did influence the Teff cell population (FIG. 2).

Figure 3A:
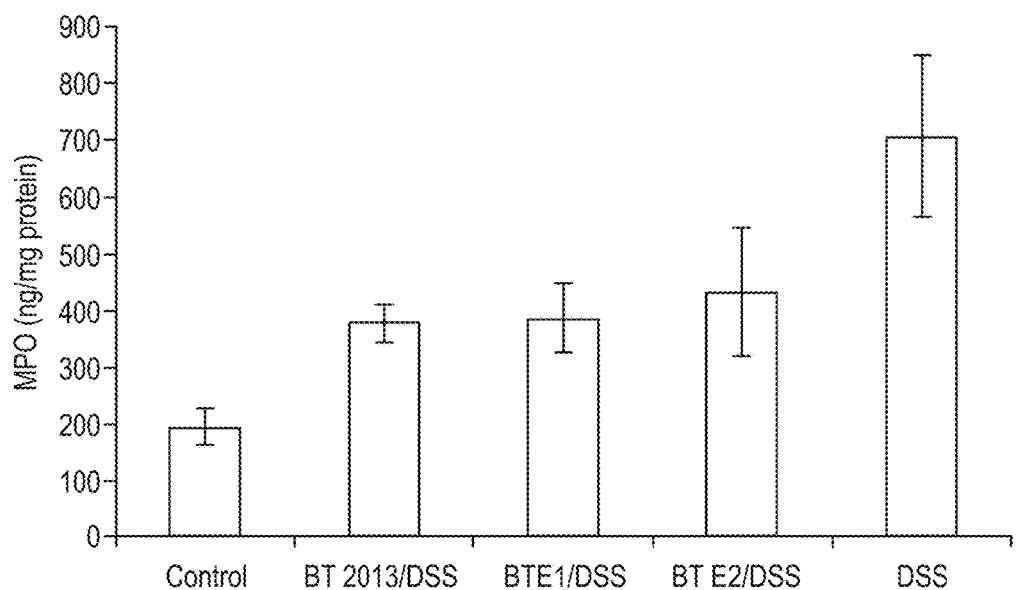
FIGS. 3A and 3B: illustrate the myeloperoxidase (MPO) activity in ileum (FIG. 3A) and caecum (FIG. 3B) of mice dosed with DSS with or without a daily intake of *B. thetaiotaomicron*
Figure 3B:
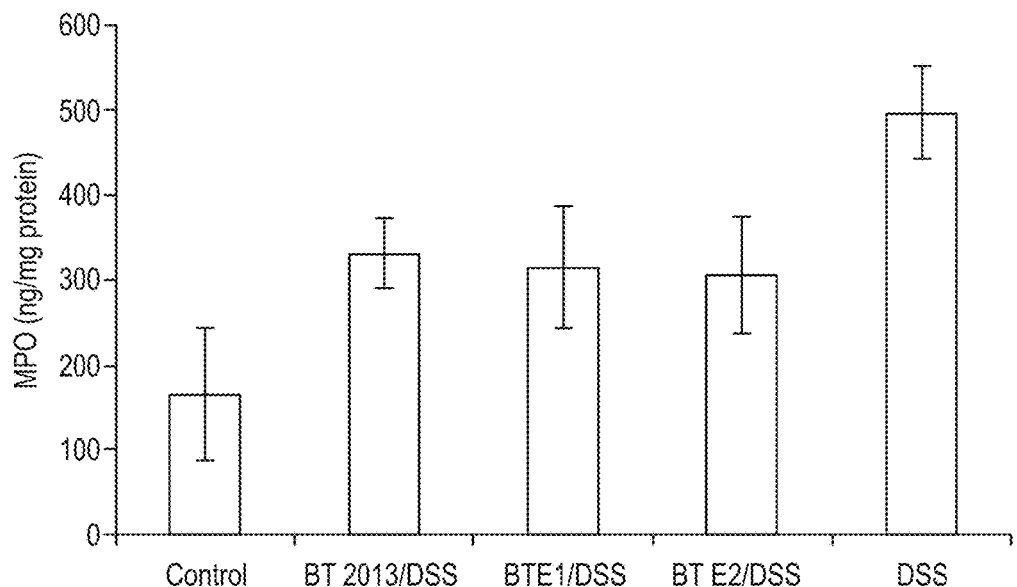

The enzymatic activity of MPO in the ileum and caecum was determined (FIGS. 3a and 3b). MPO is a proinflammatory enzyme stored in the azurophilic granules of neutrophilic granulocytes. MPO is used as an indicator of inflammation, specifically neutrophil recruitment and accumulation. The lower levels of MPO activity detected in ileal or caecal tissue samples from the *B. thetaiotaomicron*/DSS treated mice compared to DSS alone indicates a reduction in neutrophil recruitment and therefore a reduction in inflammation.

Figure 4A:
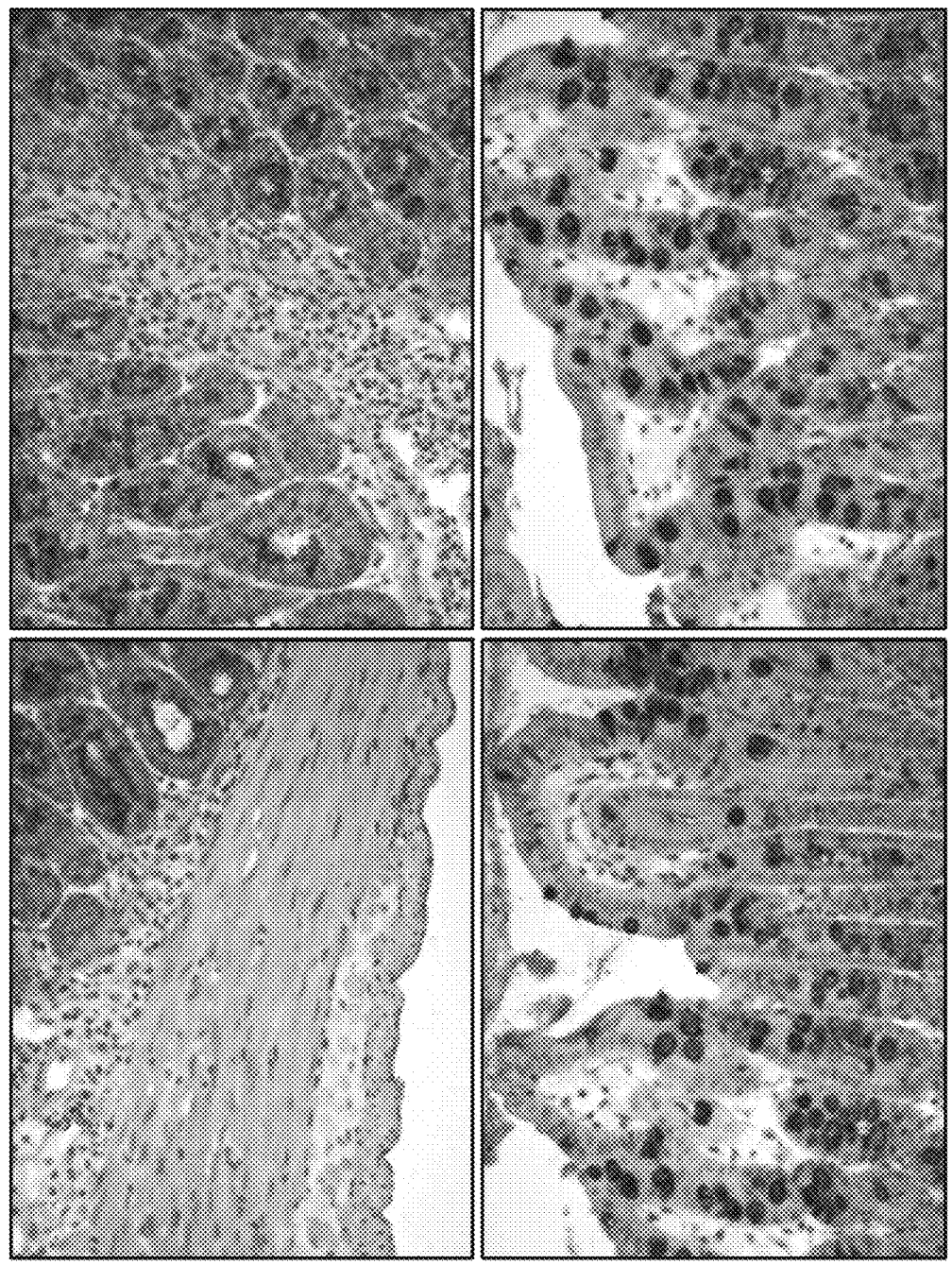
FIGS. 4A and 4B: illustrate histopathology in ascending colon of female C57131/6 mice dosed with DSS (FIG. 4A) or DSS and *B. thetaiotaomicron* (FIG. 4B)
Figure 4B:
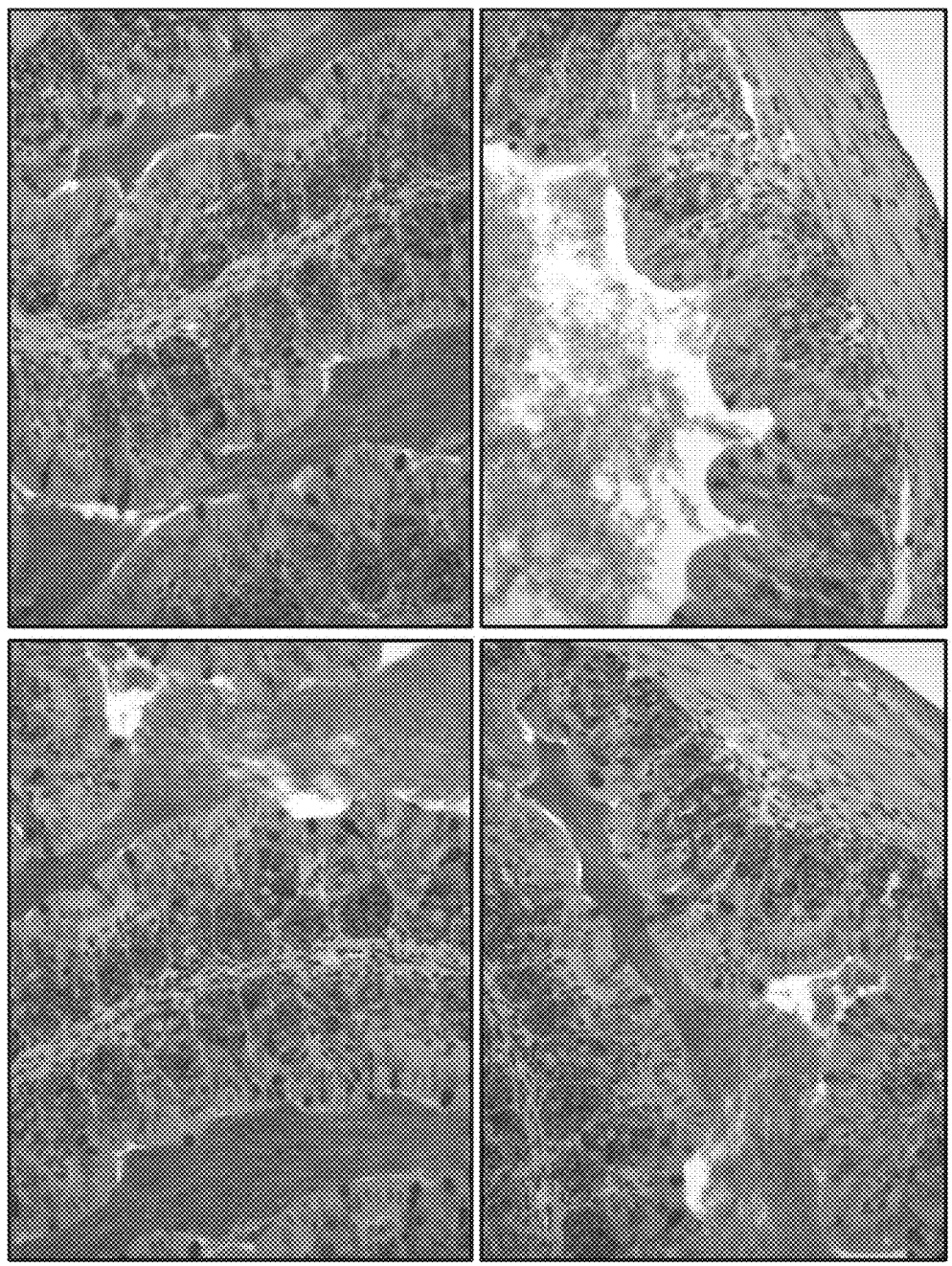
Figure 5:
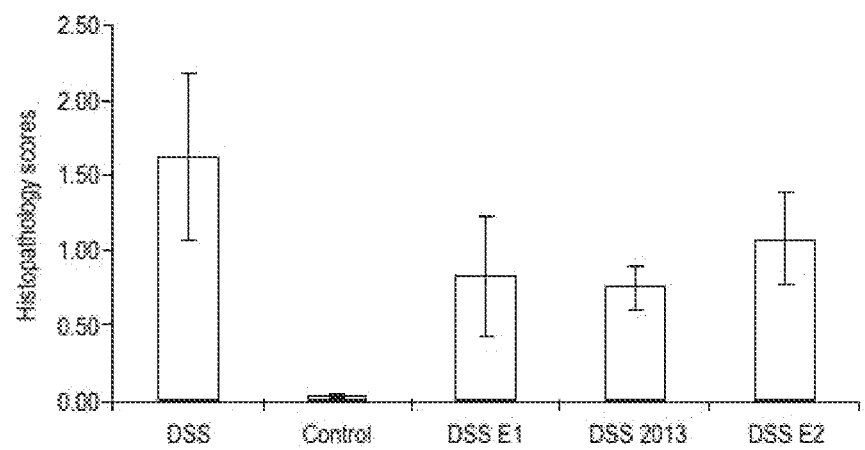
FIG. 5: illustrates the mean histopathological tissue scores for the ascending colon from mice colonised with *B. thetaiotaomicron* strains E1 and BT2013 during DSS-induced colitis.

Histological analysis of ascending colon was carried out (FIGS. 4A, 4B, and 5 and Table 1). The histopathology grading scheme was based on the criteria of Berg et al 1996, as summarised:

0=Shallow crypts, no or few infiltrating inflammatory cells, intact epithelium, goblet cells appear full of mucin. ie no pathology 1=Crypts may exhibit slight epithelial cell hyperplasia, some diffuse infiltrating inflammatory cells may be seen between crypts, luminal epithelium appears intact, goblet cells may appear slightly depleted of mucin.

2=Crypts appear deeper with distinct evidence of epithelial hyperplasia, depletion of mucin from goblet cells, infiltrating inflammatory cells evident and may be multifocal in nature, though the infiltrates are not seen in the submucosa.

3=Lesions involved a larger area of the mucosa and/or were more frequent than that seen in grade 2. The lesions did not involve the submucosa.

The luminal epithelial cells exhibited small erosions. The lesions are not transmural.

4=Crypt epithelium appears eroded. Abscesses may be present.

Luminal epithelial cells appear irregular, sometimes with complete loss.

Transmural infiltrate is observed—this was often associated with complete loss of epithelial cells into the lumen.

Figure 6:
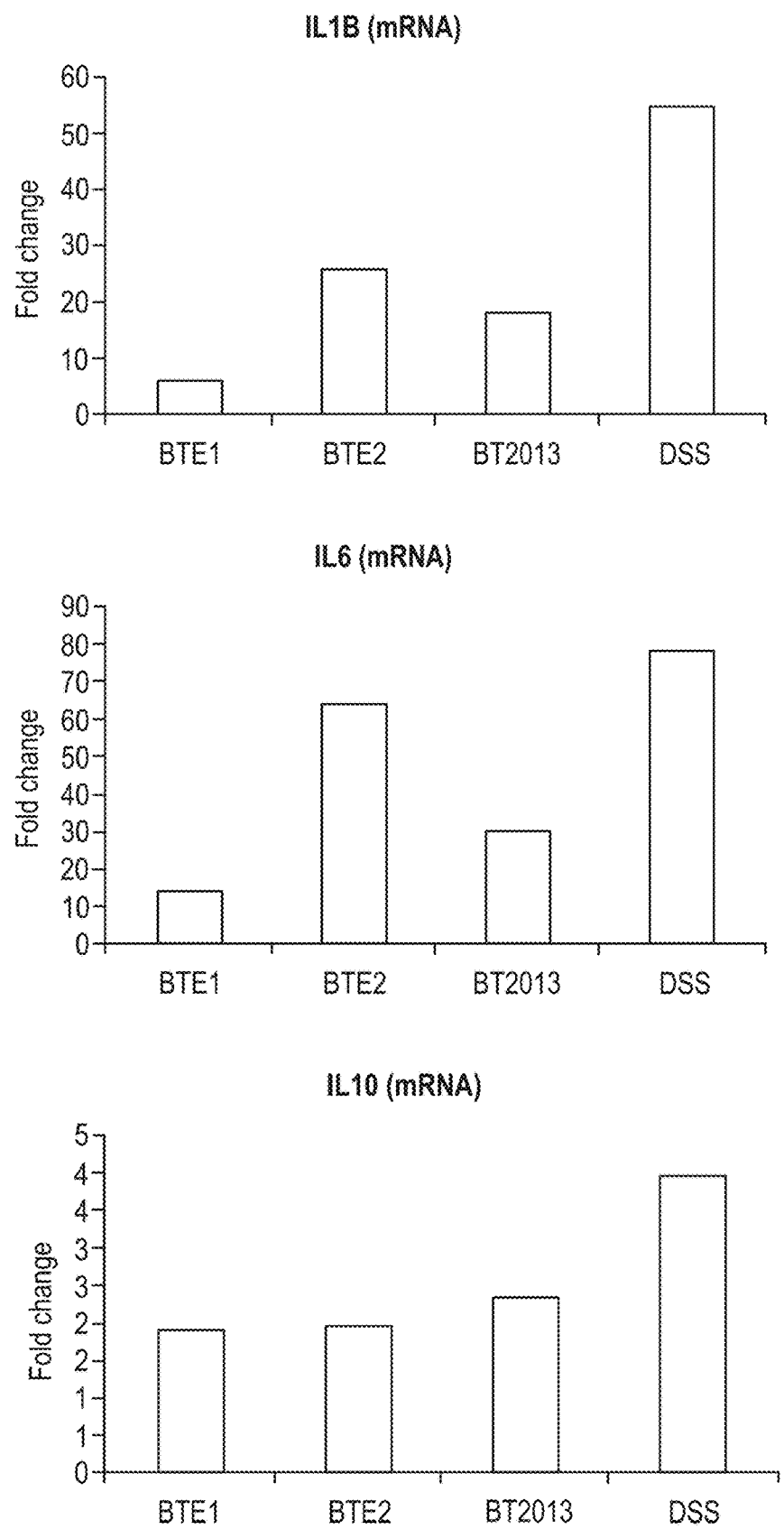
FIG. 6: illustrates the expression of proinflammatory genes (IL-1β and IL-6) and anti-inflammatory gene (IL-10) in the ascending colon of mice treated with *B. thetaiotaomicron* strains E1, E2 and BT2013.

The disruption to the colon as a result of DSS induced colitis was significantly reduced by treatment of mice with *B. thetaiotaomicron* strains E1, E2 and BT2013. The expression of inflammation-associated genes in the ascending colon was reduced in mice colonised with *B. thetaiotaomicron* compared to mice treated with DSS alone. The strains E1 and BT2013 greatly reduced IL1B and IL6 inflammatory gene expression compared to strain E2. (FIG. 6)

TABLE 1

| TTEST | CONTROL | BT E1 | BT 2013 | BT E2 |
|---|---|---|---|---|
| DSS | 0.000 | 0.032 | 0.041 | 0.089 |

In Vitro Model

Figure 7:
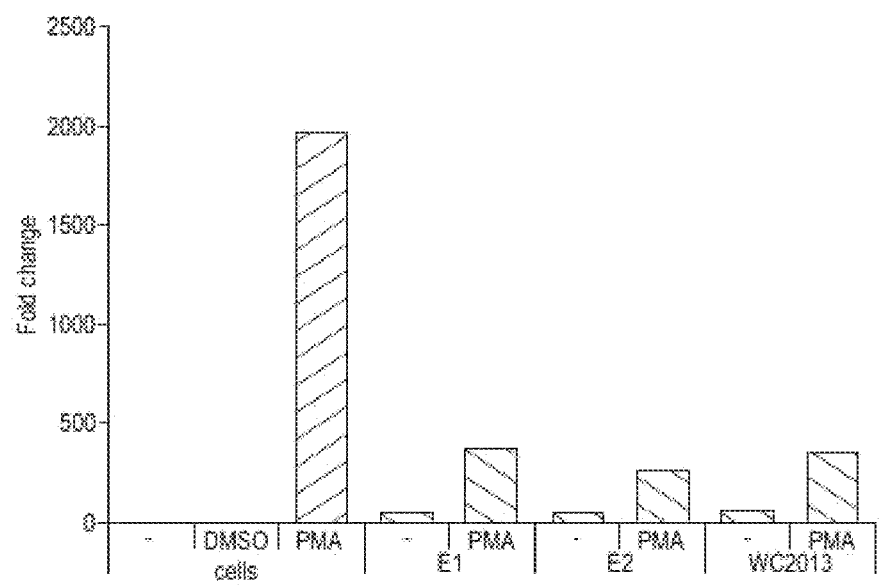
FIG. 7: illustrates the expression of IL-8 in Caco-2 cells incubated with PMA and medium or bacterial cells E1, E2 and BT2013.

The expression of the inflammatory gene interleukin-8 induced in intestinal epithelial cells after PMA exposure was modulated in the presence of *B. thetaiotaomicron* strains E1, E2 and BT2013 (FIG. 7).

Sequencing of Strain BT2013 Genome

A DNA sample from strain BT2013 was subjected to sequencing on MiSeq (v2 nano 2×250 bp) using a Nextera XT library for fast fragmentation and tagging with sequencing adaptors, to give a total of 4605120 reads (1115615927 bases).

The data analysis is summarised below:
a. Mapping to reference sequence (NC_004663 and NC_004703) using bowtie2 (2.2.2)
b. SNV and small InDel calling using VarScan (2.3.7) and SNVer (0.5.3) performing a consensus call to avoid false positives
c. Annotation of variations using reference gff
d. Large InDel calling using pindel (0.2.5a3)
e. De-novo assembly of unmapped reads using SOAPdenovo (2.04)
f. Blast of assembled contigs against NCBI nt database
g. Subsampling of all reads of the sample to 50%
h. De-novo assembly on the subsampled reads using SOAPdenovo (2.04)

The sequences were mapped to the reference sequence (NC_004663 and NC_004703) using bowtie2 (2.2.2). Nucleotide variations and small insertions and/or deletions were identified using VarScan (2.3.7) and SNVer (0.5.3) to avoid false positives during sequencing and variations were annotated using a reference sequence. Large insertions and deletions were identified using pindel (0.2.5a3). Unmapped reads were assembled de novo using SOAPdenovo (2.04). The sequencing fragments were reassembled into contigs which were blasted against the NCBI nucleotide database. All the reads of the sample were subsampled to 50% and were then assembled de novo using SOAPdenovo (2.04) to provide a concatenated version of the de novo sequence assembly of BT2013.

Sequences SEQ ID NO:1 (concatenated version of the de novo sequence assembly of BT2013)—see electronic sequence listing.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10226489B2). An electronic copy of the "Sequence Listing" will also be available from the USPTO upon request and payment of the fee set forth in 37 CFR 1.19(b)(3).

The invention claimed is:

1. A pharmaceutical composition that comprises:
(a) an amount of a *Bacteroides thetaiotaomicron* bacteria strain deposited under accession number NCIMB 42341, wherein said amount comprises from about $1\times10^3$ to about $1\times10^{12}$ CFU/g of said *Bacteroides thetaiotaomicron* bacteria strain with respect to the total weight of the pharmaceutical composition, wherein the *Bacteroides thetaiotaomicron* bacteria strain is live and viable; and
(b) a pharmaceutically acceptable excipient, carrier or diluent;
wherein said pharmaceutical composition is a lyophilized composition.

2. The pharmaceutical composition of claim 1, wherein said pharmaceutical composition strain is encapsulated.

3. The pharmaceutical composition of claim 1, wherein said pharmaceutical composition is formulated for oral delivery.

4. The pharmaceutical composition of claim 3, wherein said pharmaceutical composition comprises an enteric coating.

5. The pharmaceutical composition of claim 1, wherein said amount comprises from about $1\times10^6$ to about $1\times10^{12}$ CFU/g of said *Bacteroides thetaiotaomicron* bacteria strain with respect to a total weight of the pharmaceutical composition.

6. The pharmaceutical composition of claim 1, wherein said pharmaceutical composition further comprises at least one prebiotic compound.

7. The pharmaceutical composition of claim 6, wherein said at least one prebiotic compound is selected from the group consisting of, inulin, a transgalacto-oligosaccharide, a fructo-oligosaccharide, a chitosan-oligosaccharide, an isomaltooligosaccharide, a pectin, a xylo-oligosaccharide, a beta-glucan, an arable gum modified starch, polydextrose, D-tagatose, acacia fiber, carob, oats, a citrus fiber, and any combination thereof.

8. The pharmaceutical composition of claim 1, wherein said amount comprises from about $1\times10^8$ to about $1\times10^{10}$ CFU/g of said *Bacteroides thetaiotaomicron* bacteria strain with respect to a total weight of the pharmaceutical composition.

9. The pharmaceutical composition of claim 1, in the form of a tablet, capsule or powder.

10. The pharmaceutical composition of claim 1, further comprising an additional bacteria strain.

11. The pharmaceutical composition of claim 10, wherein the additional bacteria strain is *Roseburia hominis*.

12. The pharmaceutical composition of claim 1, wherein said pharmaceutical composition is formulated for enteral delivery.

13. The pharmaceutical composition of claim 1, wherein said pharmaceutical composition is formulated for rectal delivery.

14. The pharmaceutical composition of claim 1, comprising the pharmaceutically acceptable carrier, wherein the pharmaceutically acceptable carrier is lactose, starch, glucose, methyl cellulose, magnesium stearate, mannitol, or sorbitol.

* * * * *

UNITED STATES PATENT AND TRADEMARK OFFICE
CERTIFICATE OF CORRECTION

| | |
|---|---|
| PATENT NO. | : 10,226,489 B2 |
| APPLICATION NO. | : 15/631945 |
| DATED | : March 12, 2019 |
| INVENTOR(S) | : Angela Margaret Patterson, George Grant and Imke Mulder |

Page 1 of 1

It is certified that error appears in the above-identified patent and that said Letters Patent is hereby corrected as shown below:

On the Title Page

Item (30), Foreign Application Priority Data, please insert:
--(30) Foreign Application Priority Data
Dec. 23, 2014 (GB).......1423084.1--

Signed and Sealed this
Seventeenth Day of November, 2020

Andrei Iancu
*Director of the United States Patent and Trademark Office*